United States Patent
Oba et al.

(10) Patent No.: US 12,195,050 B2
(45) Date of Patent: Jan. 14, 2025

(54) DRIVER EYEBALL BEHAVIOR INFORMATION PROCESSING APPARATUS, PROCESSING SYSTEM, PROCESSING METHOD, AND PROCESSING PROGRAM

(71) Applicant: Sony Semiconductor Solutions Corporation, Kanagawa (JP)

(72) Inventors: Eiji Oba, Tokyo (JP); Kohei Kadoshita, Tokyo (JP)

(73) Assignee: Sony Semiconductor Solutions Corporation, Kanagawa (JP)

(*) Notice: Subject to any disclaimer, the term of this patent is extended or adjusted under 35 U.S.C. 154(b) by 243 days.

(21) Appl. No.: 17/791,844

(22) PCT Filed: Dec. 17, 2020

(86) PCT No.: PCT/JP2020/047114
§ 371 (c)(1),
(2) Date: Jul. 8, 2022

(87) PCT Pub. No.: WO2021/145131
PCT Pub. Date: Jul. 22, 2021

(65) Prior Publication Data
US 2023/0054024 A1    Feb. 23, 2023

(30) Foreign Application Priority Data
Jan. 17, 2020   (JP) .................... 2020-006096

(51) Int. Cl.
*B60W 60/00*    (2020.01)
*A61B 5/16*     (2006.01)
(Continued)

(52) U.S. Cl.
CPC ......... *B60W 60/0053* (2020.02); *A61B 5/165* (2013.01); *A61B 5/18* (2013.01);
(Continued)

(58) Field of Classification Search
CPC ........... B60W 60/0053; B60W 50/082; B60W 2556/40; B60W 2540/00; A61B 5/165; A61B 5/18
See application file for complete search history.

(56) References Cited

U.S. PATENT DOCUMENTS

| | | | |
|---|---|---|---|
| 2018/0148071 A1* | 5/2018 | Kim | .................. B60W 60/0059 |
| 2019/0143989 A1 | 5/2019 | Oba | |
| 2019/0318181 A1 | 10/2019 | Katz et al. | |

FOREIGN PATENT DOCUMENTS

| | | |
|---|---|---|
| CN | 107207013 A | 9/2017 |
| CN | 109844842 A | 6/2019 |

(Continued)

OTHER PUBLICATIONS

English Translation of CN 109074748 A Author: Oba, Eiji Title: Image Processing Apparatus, Image Processing Method and Movable Body Date: Dec. 21, 2018 (Year: 2018).*

(Continued)

*Primary Examiner* — James J Lee
*Assistant Examiner* — Steven Vu Nguyen
(74) *Attorney, Agent, or Firm* — Wolf, Greenfield & Sacks, P.C.

(57) ABSTRACT

There is provided an information processing apparatus including an eyeball behavior analysis unit (300) that analyzes an eyeball behavior of a driver who drives a moving object, in which the eyeball behavior analysis unit dynamically switches an analysis mode according to a driving mode of the moving object.

13 Claims, 11 Drawing Sheets

(51) Int. Cl.
A61B 5/18 (2006.01)
B60W 50/08 (2020.01)

(52) U.S. Cl.
CPC ....... B60W 50/082 (2013.01); *B60W 2540/00* (2013.01); *B60W 2556/40* (2020.02)

(56) References Cited

FOREIGN PATENT DOCUMENTS

| | | |
|---|---|---|
| JP | 2005323180 A | 11/2005 |
| JP | 2009205386 A | 9/2009 |
| JP | 2012-226635 A | 11/2012 |
| JP | 2015-127937 A | 7/2015 |
| JP | 2016-088497 A | 5/2016 |
| JP | 2017023519 A | 2/2017 |
| JP | 2018151910 A | 9/2018 |
| JP | 2019-091205 A | 6/2019 |
| JP | 2019-136165 A | 8/2019 |
| JP | 2019-533209 A | 11/2019 |
| WO | WO 2017/195405 A1 | 11/2017 |
| WO | WO-2019017216 A1 | 1/2019 |
| WO | WO 2019/082774 A1 | 5/2019 |
| WO | WO 2019/097944 A1 | 5/2019 |
| WO | WO 2019/188398 A1 | 10/2019 |
| WO | WO 2019/202881 A1 | 10/2019 |

OTHER PUBLICATIONS

English Translation of JP 2018151910 A Title: Device for Determining Degree of Concentration, Method for Determining Degree of Concentration, and Program for Determining Degree of Concentration Author: Yabuuchi et al. (Year: 2018) Date: Sep. 27, 2018.*
International Search Report and English translation thereof mailed Mar. 9, 2021 in connection with International Application No. PCT/JP2020/047114.
International Written Opinion and English translation thereof mailed Mar. 9, 2021 in connection with International Application No. PCT/JP2020/047114.
International Preliminary Report on Patentability and English translation thereof mailed Jul. 28, 2022 in connection with International Application No. PCT/JP2020/047114.

* cited by examiner

*FIG. 1*

| AUTONOMOUS DRIVING LEVEL | NAME | | SUBJECT OF EXECUTION OF DRIVING TASK | SUBJECT OF MONITORING FOR SAFE DRIVING |
|---|---|---|---|---|
| 0 | MANUAL DRIVING (DIRECT DRIVING STEERING) | NO DRIVING SUPPORT | DRIVER | DRIVER |
| 1 | MANUAL DRIVING (DIRECT DRIVING STEERING) | DRIVING SUPPORT (AUTOMATIC BRAKING, ACC, LKAS, AND THE LIKE) | DRIVER | DRIVER |
| 2 | AUTONOMOUS DRIVING FUNCTION UNDER SPECIFIC CONDITION | | DRIVER (PARTIALLY SYSTEM) | DRIVER |
| 3 | CONDITIONAL AUTONOMOUS DRIVING | | SYSTEM | SYSTEM (PARTIALLY DRIVER) |
| 4 | FULLY AUTONOMOUS DRIVING UNDER SPECIFIC CONDITION | | SYSTEM | SYSTEM |

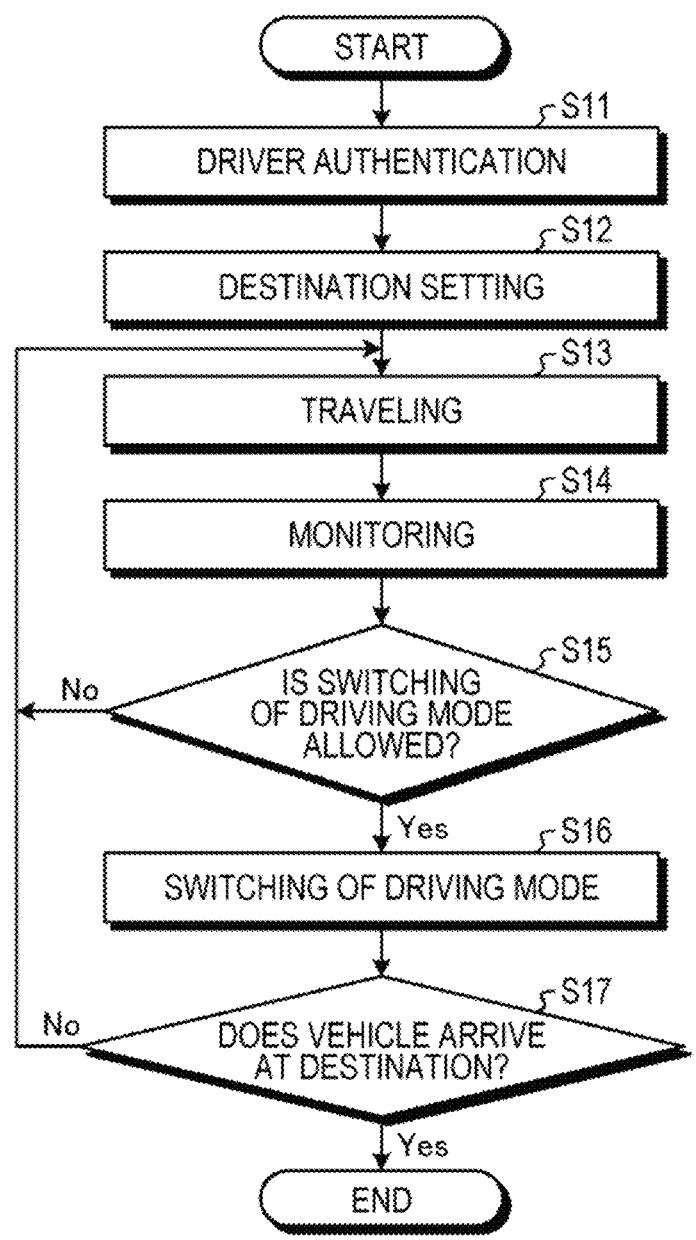

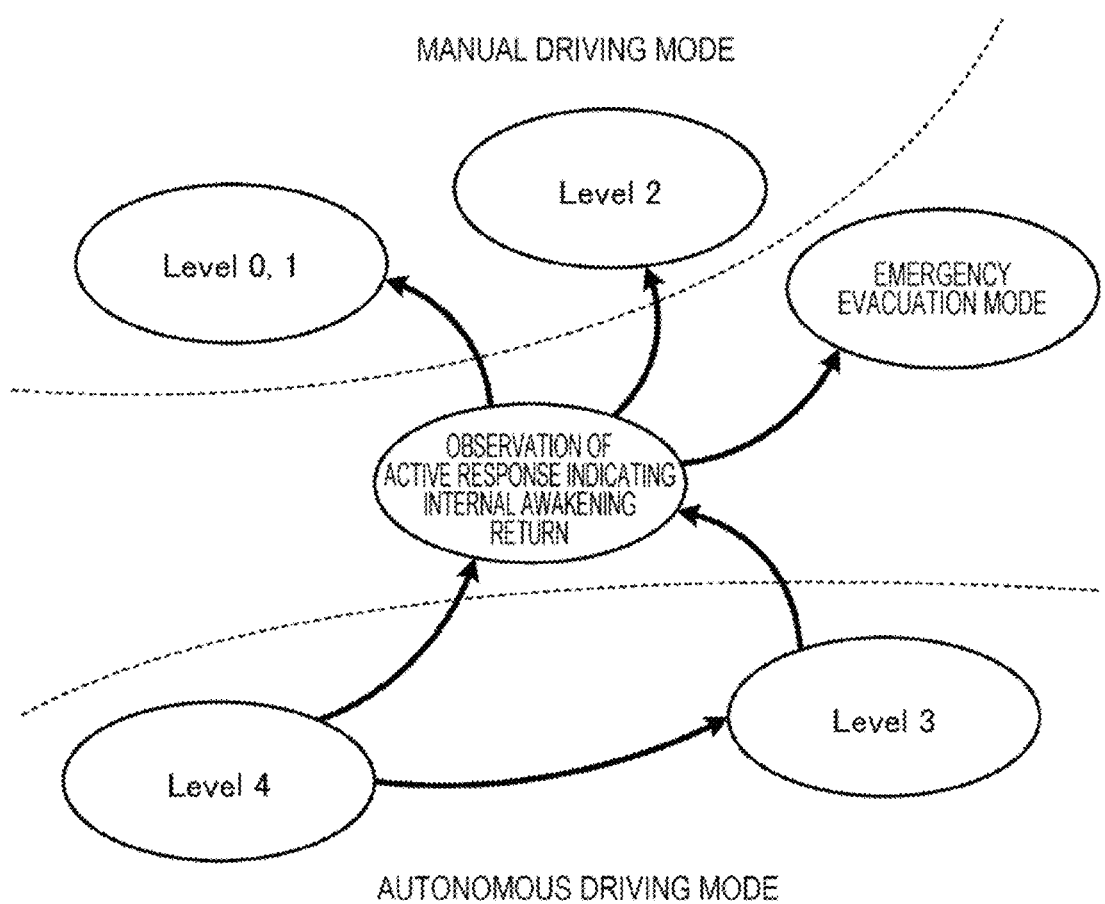

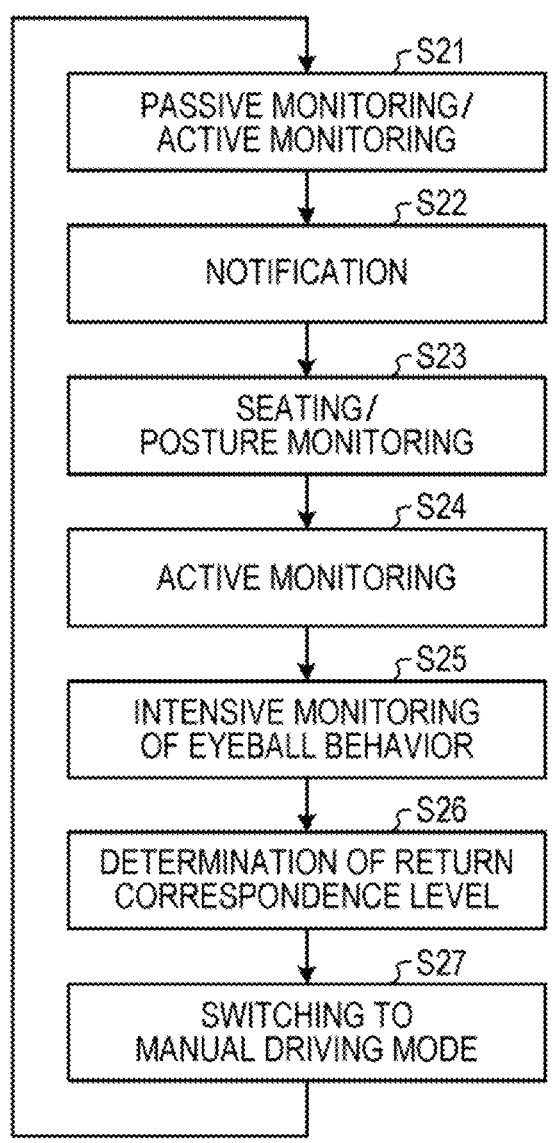

DRIVER EYEBALL BEHAVIOR INFORMATION PROCESSING APPARATUS, PROCESSING SYSTEM, PROCESSING METHOD, AND PROCESSING PROGRAM

CROSS-REFERENCE TO RELATED APPLICATIONS

This application claims the benefit under 35 U.S.C. § 371 as a U.S. National Stage Entry of International Application No. PCT/JP2020/047114, filed in the Japanese Patent Office as a Receiving Office on Dec. 17, 2020, which claims priority to Japanese Patent Application Number 2020-006096, filed in the Japanese Patent Office on Jan. 17, 2020, each of which is hereby incorporated by reference in its entirety.

TECHNICAL FIELD

The present disclosure relates to an information processing apparatus, an information processing system, an information processing method, and an information processing program.

BACKGROUND ART

Recently, an autonomous driving technique of controlling a vehicle by a vehicle control system (information processing system) has been actively developed. However, even in a case where such an autonomous driving technique has become widespread, it is expected that there may be a situation where an autonomous driving allowance section and a manual driving allowance section are mixed depending on an actual road infrastructure maintenance situation, the autonomous driving allowance section being a road section in which the system can independently perform autonomous driving control, and the manual driving allowance section being a road section in which autonomous driving is not allowed. That is, not only may there be a situation where autonomous driving traveling is continuously performed by the system in a completely independent manner, but also there may be a situation where switching from an autonomous driving mode as described above to a manual driving mode in which a driver performs steering needs to be performed.

Then, in switching from the autonomous driving mode to the manual driving mode, in order to avoid an accident or the like being caused, it is desirable that the system determines a return correspondence level of the driver to the manual driving mode and the switching is executed only in a case where it is determined that a return to the manual driving is allowed. Therefore, for example, it is considered that the system detects an awakening level of the driver by analyzing an eyeball behavior and uses means for determining a return correspondence level to the manual driving mode as one of means for determining the return correspondence level, the eyeball behavior being considered as one in which activity results of the human brain such as cognitive results are reflected. Then, in recent years, with the advancement of image analysis techniques, it has become relatively easy to detect an eyeball behavior with high accuracy by analyzing a captured image of an eyeball. For example, in a technique described in Patent Document 1 below, an eyeball behavior of a driver is observed by an image capturing device.

Moreover, the above-described eyeball behavior not only has common tendencies for each of individuals according to a state (for example, drowsy feeling) but also reflects activities in the brain. Thus, the eyeball behavior is also affected by driver's own innate tendencies and a driver's unique experience. That is, the eyeball behavior indicates a specified behavior for each person. Therefore, in a case where it is desired to accurately determine the awakening level of the driver by analyzing the eyeball behavior, the vehicle control system is required to constantly recognize and learn the eyeball behavior that is specified for each driver.

CITATION LIST

Patent Document

Patent Document 1: Japanese Patent Application Laid-Open No. 2015-127937
Patent Document 2: WO 2019/188398 A
Patent Document 3: WO 2019/097944 A
Patent Document 4: WO 2019/202881 A
Patent Document 5: WO 2019/082774 A

SUMMARY OF THE INVENTION

Problems to be Solved by the Invention

On the other hand, the eyeball behavior such as a microsaccade and a tremor is a high-speed movement. For this reason, in a case where it is desired to detect such an eyeball behavior with high accuracy, it is required to perform sampling and analysis at a high frame rate (for example, 250 frames per second (fps)). Note that a microsaccade refers to a high-speed jumping movement of the eyeball that is unconsciously performed and is observed as an involuntary small eye jerk in a case where a person is looking at an object. However, in a case where such high-speed sampling and analysis are constantly performed by the vehicle control system (information processing system), a load in imaging processing, analysis processing, and the like is increased. This leads to an increase in power consumption and an increase in device temperature due to high-speed driving. Moreover, in such a case, noise generated by a temperature increase also causes a decrease in detection sensitivity.

Therefore, the present disclosure proposes an information processing apparatus, an information processing system, an information processing method, and an information processing program capable of accurately determining a return correspondence level of a driver while reducing a load in imaging processing, analysis processing, and the like.

Solutions to Problems

According to the present disclosure, there is provided an information processing apparatus including: an eyeball behavior analysis unit that analyzes an eyeball behavior of a driver who is driving a moving object, in which the eyeball behavior analysis unit dynamically switches an analysis mode according to a driving mode of the moving object.

Furthermore, according to the present disclosure, there is provided an information processing system including: an eyeball behavior analysis unit that analyzes an eyeball behavior of a driver who drives a moving object, in which the eyeball behavior analysis unit dynamically switches an analysis mode according to a driving mode of the moving object.

Furthermore, according to the present disclosure, there is provided an information processing method including: analyzing, via an eyeball behavior analysis unit, an eyeball behavior of a driver who drives a moving object, in which an analysis mode of the analysis is dynamically switched according to a driving mode of the moving object.

Furthermore, according to the present disclosure, there is provided an information processing program causing a computer to execute: an analysis function of analyzing an eyeball behavior of a driver who drives a moving object, in which an analysis mode of the analysis function is dynamically switched according to a driving mode of the moving object.

BRIEF DESCRIPTION OF DRAWINGS

FIG. 1 is an explanatory diagram illustrating an example of autonomous driving levels.

FIG. 2 is a flowchart illustrating an example of traveling according to an embodiment of the present disclosure.

FIG. 3 is an explanatory diagram illustrating an example of a transition of an autonomous driving level according to the embodiment of the present disclosure.

FIG. 4 is a flowchart illustrating an example of a monitoring operation according to the embodiment of the present disclosure.

MODE FOR CARRYING OUT THE INVENTION

Figure 5:
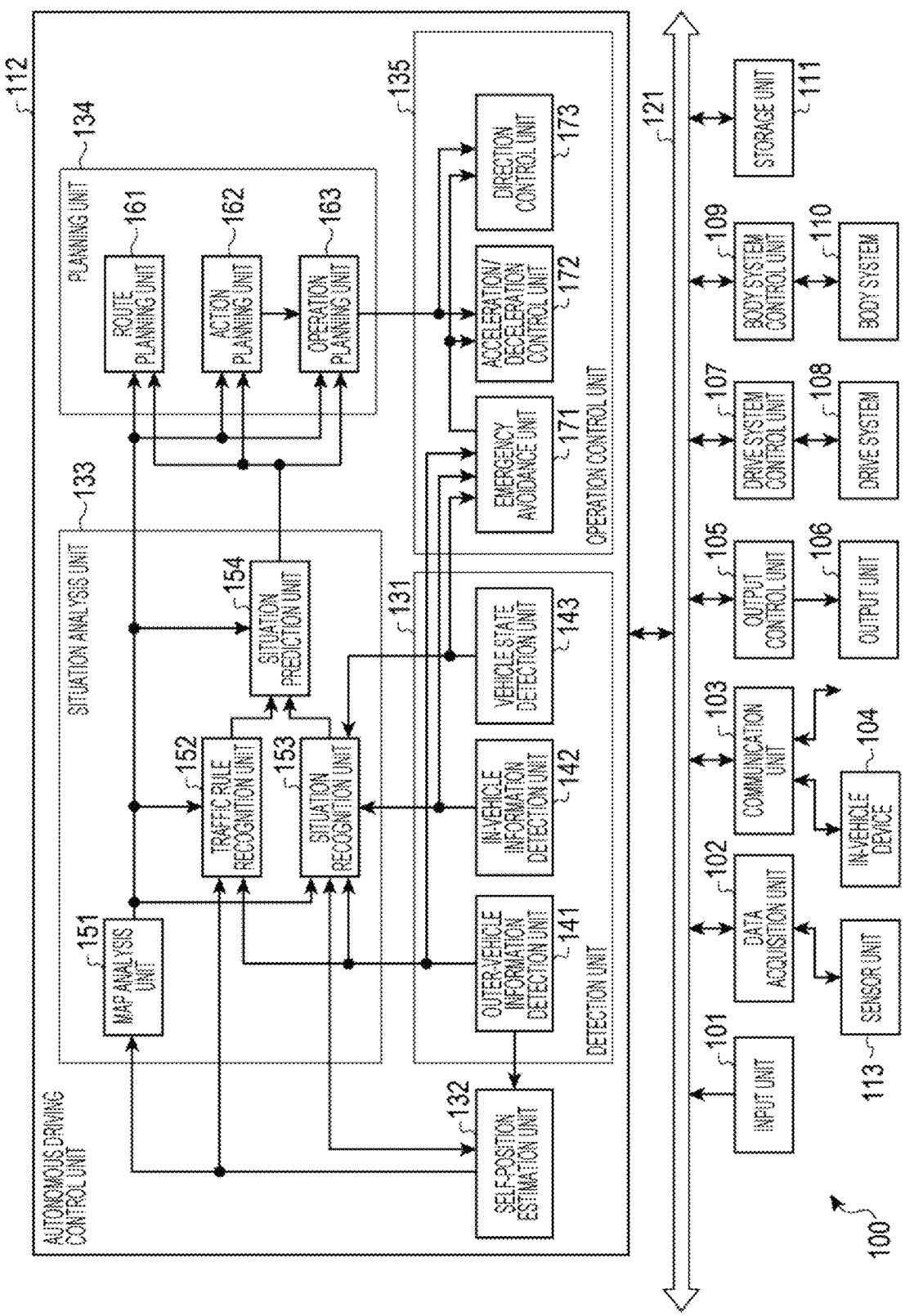
FIG. 5 is an explanatory diagram illustrating an example of a detailed configuration of a vehicle control system 100 according to the embodiment of the present disclosure.

Hereinafter, preferred embodiments of the present disclosure will be described in detail with reference to the accompanying drawings. Note that, in the present specification and the drawings, components having substantially same functional configurations are denoted by same reference numerals, and repeated description thereof is omitted.

Note that description will be given in a following order.
1. Example of Autonomous Driving Level
2. Example of Traveling
3. Example of Transition of Autonomous Driving Level
4. Example of Monitoring
5. Background Leading to Embodiments of Present Disclosure
6. Embodiments
6.1 Detailed Configuration of Vehicle Control System 100
6.2 Detailed Configuration of Sensor Unit 113
6.3 Detailed Configuration of Unit for Executing Determination of Awakening Level of Driver
6.4 Operation Example of Eyeball Behavior Analysis Unit 300
6.5 Information Processing Method
6.6 Summary
7. Hardware Configuration
8. Supplement 1. Example of Autonomous Driving Level First, before describing details of an embodiment of the present disclosure, an autonomous driving level of an autonomous driving technique will be described with reference to FIG. 1. FIG. 1 is an explanatory diagram illustrating an example of autonomous driving levels. FIG. 1 illustrates an autonomous driving level defined by the Society of Automotive Engineers (SAE). Note that the following description will be basically given with reference to the autonomous driving level defined by the above-described SAE. Here, in examination of the autonomous driving level illustrated in FIG. 1, a problem and a reliability in a case where an autonomous driving technique has widely spread are not thoroughly examined. For this reason, in the following description, there are some parts that are not necessarily described by interpretation as defined in the SAE on the basis of the problem and the like.

As illustrated in FIG. 1, the autonomous driving levels are classified into, for example, five levels from a level 0 to a level 4. First, an autonomous driving level 0 corresponds to manual driving without driving support by a vehicle control system (direct driving steering of a driver), and a driver executes all driving tasks and also executes monitoring for safe driving (for example, an action of avoiding a danger).

Next, an autonomous driving level 1 corresponds to manual driving (direct driving steering) in which driving support (automatic braking, adaptive cruise control (ACC), lane keeping assistant system (LKAS), and the like) by the vehicle control system can be executed, and a driver executes all driving tasks and also executes monitoring for safe driving.

Next, an autonomous driving level 2 is also referred to as an "autonomous driving function under a specific condition", and the vehicle control system executes a subtask of a driving task related to a vehicle control in both a front-rear direction and a left-right direction of a vehicle under a specific condition. For example, in the autonomous driving level 2, the vehicle control system controls both a steering operation and acceleration/deceleration in cooperation (for example, cooperation between ACC and LKAS). On the other hand, even in the autonomous driving level 2, a subject of an execution of a driving task is basically a driver, and a subject of monitoring for safe driving is also a driver.

Furthermore, an autonomous driving level 3 is also referred to as "conditional autonomous driving", and the vehicle control system can execute all driving tasks within a limited range. In the autonomous driving level 3, a subject of an execution of a driving task is the vehicle control system, and a subject of monitoring for safe driving is also basically the vehicle control system.

On the other hand, in the autonomous driving level 3 defined by the SAE, a type of a secondary task that can be actually executed by a driver (here, a "secondary task" means an operation other than a driving operation performed by a driver during traveling) is not clearly defined. Specifically, it is considered that a driver can perform a work or an action other than steering, for example, a secondary task such as an operation of a mobile terminal, a telephone conference, watching videos, a game play, thinking, or having a conversation with another occupant during traveling in the autonomous driving level 3. On the other hand, in a range of the definition of the autonomous driving level 3 by the SAE, it is expected that a driver appropriately performs a response such as a driving operation according to a request or the like from the vehicle control system due to a system failure, a deterioration of a traveling environment, or the like. Therefore, in the autonomous driving level 3, in order to ensure safe traveling, even in a situation where a secondary task as described above is being executed, it is expected that a driver is constantly in a preparation state in which the driver can immediately return to manual driving.

Moreover, an autonomous driving level 4 is also referred to as "fully autonomous driving under a specific condition", and the vehicle control system executes all driving tasks within a limited range. In the autonomous driving level 4, a subject of an execution of a driving task is the vehicle control system, and a subject of monitoring for safe driving is also the vehicle control system. On the other hand, unlike the autonomous driving level 3 described above, in the autonomous driving level 4, it is not expected that a driver performs a response such as a driving operation (manual driving) or the like according to a request or the like from the vehicle control system due to a system failure or the like. Therefore, in the autonomous driving level 4, a driver can perform a secondary task as described above, and for example, can take a nap depending on a situation.

As described above, in the autonomous driving level 0 to the autonomous driving level 2, a vehicle travels in a manual driving mode in which a driver is a subject of an execution of all or some of the driving tasks. Therefore, in these three autonomous driving levels, a driver is not allowed to engage in a secondary task that is an action other than manual driving and an operation related to manual driving, the secondary task causing a decrease in attention of a driver and causing inattention with respect to in front of a driver during traveling.

On the other hand, in the autonomous driving level 3, a vehicle travels in the autonomous driving mode in which the vehicle control system is a subject of an execution of all the driving tasks. On the other hand, as described above, in the autonomous driving level 3, there may be a situation where a driver performs a driving operation. Therefore, in the autonomous driving level 3, in a case where a driver is allowed to perform a secondary task, the driver is required to be in a preparation state in which a driver can return from a secondary task to manual driving.

Moreover, in the autonomous driving level 4, a vehicle travels in the autonomous driving mode in which the vehicle control system executes all the driving tasks. On the other hand, there may be a section in which the autonomous driving level 4 cannot be applied to a part of a traveling route due to a maintenance situation of an actual road infrastructure or the like. In such a section, for example, since it is assumed that the autonomous driving level of 2 or lower is set, a driver is required to autonomously execute the driving task. For this reason, even in the autonomous driving level 4, since there is a transition to the autonomous driving level of 2 or lower as described above, a driver is required to be in a preparation state in which a driver can return from a secondary task to manual driving.

Note that an actual use range for each of the autonomous driving levels different from each other is referred to as an "operation design domain (ODD)", the actual use range being allowed for each of the autonomous driving levels.

2. Example of Traveling

Next, an example of traveling according to an embodiment of the present disclosure will be described with reference to FIG. 2 on the basis of the autonomous driving level described above. FIG. 2 is a flowchart illustrating an example of traveling according to an embodiment of the present disclosure. As illustrated in FIG. 2, in traveling according to the embodiment of the present disclosure, the vehicle control system executes, for example, steps from step S11 to step S17. Details of each of these steps will be described below.

First, the vehicle control system executes driver authentication (step S11). The driver authentication can be performed by knowledge authentication using a password, a personal identification number, or the like, biometric authentication using a face, a fingerprint, an iris of a pupil, a voiceprint, or the like, or authentication using both knowledge authentication and biometric authentication. In the embodiment of the present disclosure, by executing such driver authentication before starting traveling, even in a case where a plurality of drivers drives the same vehicle, it is possible to acquire unique biometric information or the like of each driver such as an eyeball behavior of each driver in association with each driver.

Next, a destination is set by operating, for example, an input unit 101 (refer to FIG. 5) to be described later by a driver or the like (step S12). Note that an example in which a driver boards a vehicle and sets a destination is described in the embodiment. On the other hand, the embodiment of the present disclosure is not limited thereto. The vehicle control system may preset a destination on the basis of destination information or calendar information that is manually input to a smartphone or the like (assumed to be capable of performing communication with the vehicle control system) before the driver rides the vehicle. Alternatively, the vehicle control system may automatically preset a destination by acquiring schedule information or the like stored in advance in a smartphone, a cloud server, or the like (assumed to be capable of performing communication with the vehicle control system) via a concierge service. Then, the vehicle control system performs preplanning setting such as a traveling route on the basis of a set destination. Moreover, the vehicle control system updates and acquires local dynamic map (LDM) information or the like obtained by constantly updating information of a road environment of a set traveling route or the like, that is, a traveling map information of a road on which the vehicle travels with high precision. In addition, the vehicle control system sets an autonomous driving level appropriate for each section on a traveling route on the basis of the acquired LDM information or the like.

Next, the vehicle control system starts displaying a traveling section on the traveling route. Then, the vehicle control system starts traveling according to the set autonomous driving level (step S13). Note that, in a case where traveling is started, display of the traveling section is updated on the basis of position information of the vehicle (host vehicle) and the acquired LDM update information.

Next, the vehicle control system executes monitoring (observation) of a state of the driver as appropriate (step S14). In the embodiment of the present disclosure, for example, the monitoring is executed to acquire training data for determining a return correspondence level (for example, an awakening level) of the driver, or the monitoring is executed to perform switching of the driving mode according to the autonomous driving level which is set for each section on the traveling route. Note that details of the monitoring will be described later.

Next, in a case where the vehicle reaches a switching point from the autonomous driving mode to the manual driving mode on the basis of the autonomous driving level which is set for each section on the traveling route, the vehicle control system determines whether or not the driving mode can be switched (step S15). Note that details of the determination performed at this time will be described later. Then, in a case where it is determined that the driving mode can be switched (Yes in step S15), the vehicle control system proceeds to processing of step S16, and in a case where it is determined that the driving mode cannot be switched (No in step S15), the vehicle control system returns to processing of step S13.

Next, the vehicle control system switches the driving mode (step S16). Moreover, the vehicle control system determines whether or not the vehicle (host vehicle) arrives at the destination (step S17). In a case where the vehicle arrives at the destination (Yes in step S17), the vehicle control system ends processing, and in a case where the host vehicle does not arrive at the destination (No in step S17), the vehicle control system returns to processing of step S13. Thereafter, the vehicle control system repeats processing from step S13 to step S17 as appropriate until the vehicle arrives at the destination.

3. Example of Transition of Autonomous Driving Level

Next, an example of a transition of the autonomous driving level according to the embodiment of the present disclosure will be described in more detail with reference to FIG. 3. FIG. 3 is an explanatory diagram illustrating an example of a transition of the autonomous driving level according to the embodiment of the present disclosure.

As illustrated in FIG. 3, it is assumed that switching from the autonomous driving mode (a lower region in FIG. 3) to the manual driving mode (an upper region in FIG. 3) is executed, for example, in a case where a transition is performed from sections of the autonomous driving level 3 and the autonomous driving level 4 to sections of the autonomous driving levels 0 and 1 and the autonomous driving level 2 on the traveling route.

On the other hand, it is difficult for the driver to consciously maintain a preparation state in which the driver can return to the manual driving while the vehicle travels in the autonomous driving mode. For example, while the vehicle travels in the autonomous driving mode, it is considered that the driver is immersed in a secondary task such as sleep (nap), watching television or videos, or a game play. Furthermore, for example, the driver may be looking in front of or around the vehicle as in the manual driving while only releasing his/her hand from a steering wheel, may be reading a book, or may be dozing. Then, the awakening levels (consciousness levels) of the driver differ depending on a difference between these secondary tasks.

Moreover, in a case where the driver falls into sleep during a period for which the vehicle travels in the autonomous driving mode, the driver is in a state in which a consciousness level or a determination level of the driver is lowered, that is, a state in which the awakening level is lowered. Then, since the driver cannot perform normal manual driving in a state in which the awakening level is lowered, in a case where the driving mode is switched to the manual driving mode in the state, an accident may occur in a worst case. Therefore, even in a state in which the awakening level is lowered, the driver is required to return to a high awakening state in which the driver can drive the vehicle under normal consciousness (internal awakening return state) immediately before switching to the manual driving mode. That is, in order to ensure safe traveling, switching from the autonomous driving mode to the manual driving mode is required to be executed only in a case where a state in which the driver returns to an internal awakening state can be observed.

Therefore, in the embodiment of the present disclosure, in order to avoid an accident or the like being caused, such switching of the driving mode can be executed only in a case where the driver is at the return correspondence level to the manual driving mode, that is, an active response indicating an internal awakening return (a state in which the driver returns to the internal awakening state) can be observed (illustrated in a center of FIG. 3). Furthermore, in the embodiment of the present disclosure, as illustrated in FIG. 3, in a case where an active response indicating an internal awakening return cannot be observed, the driving mode is switched to an emergency evacuation mode such as minimal risk maneuver (MRM). Note that processing such as deceleration, stop, or parking on a road, a roadside, or an evacuation space is performed in the emergency evacuation mode. Furthermore, in FIG. 3, in a transition from the autonomous driving level 4 to the autonomous driving level 3, the driving mode is not switched. Thus, an observation of an active response indicating an internal awakening return as described above is not performed. On the other hand, the present embodiment is not limited to the example illustrated in FIG. 3. In a case of a transition from the autonomous driving level 4 to the autonomous driving level 3, a transition based on an observation or an observation result as described above may be performed.

Specifically, in a case where an active response indicating an internal awakening return is not observed when performing a transition from the autonomous driving level 4 to the autonomous driving level 3, even though the driver should be obliged to return to the manual driving by a legal system, it is not always a state in which the driver can appropriately respond to a request to intervene (RTI) as a request for a return to the autonomous driving level 3 from the vehicle control system. More specifically, in response to an RTI as a request for a return to the autonomous driving level 3, it is not always possible that the driver is in a state of being returned to a brain awakening state and can return to a physical state that allows the manual driving without numbness or the like in the body. In such a case, when a transition from the autonomous driving level 4 to the autonomous driving level 3 is performed, there may be a situation beyond a design concept assumed in advance in the vehicle control system, and as a result, there may be a concern that an accident or the like is caused. Therefore, in the following present embodiment, in order to reduce the concern as described above, even in a stage in which the vehicle control system does not need to issue an RTI as a return request to the driver, in order to check a return correspondence level (for example, an awakening level) of the driver, a dummy RTI as a preventive return request may be performed as appropriate, and an active response indicating an internal awakening return of the driver may be observed.

Note that each arrow indicating a transition of the autonomous driving level illustrated in FIG. 3 indicates a direction of a transition in which switching is allowed to be automatically performed. Further, note that a transition in the opposite direction of each arrow is not recommended because the transition causes the driver to erroneously recognize a state of the vehicle control system. That is, in the vehicle control system according to the embodiment of the present disclosure, in a case where a transition of the autonomous driving level, such as automatically switching from the autonomous driving mode to the manual driving mode with an intervention of a driver, is once performed, it is desirable that the vehicle control system is designed not to automatically return to the autonomous driving mode again without an intentional instruction of a driver. As described above, providing directivity (irreversibility) in switching of the driving mode means that the vehicle control system is designed to prevent the driving mode from being switched to the autonomous driving mode without a clear intention of a driver. Therefore, according to the vehicle control system, the autonomous driving mode cannot be enabled only with a clear intention of a driver. For example, in a case where the driving mode is not the autonomous driving mode, it is possible to prevent the driver from misunderstanding that the driving mode is the autonomous driving mode and performing an action such as easily starting a secondary task.

As described above, in the embodiment of the present disclosure, in order to ensure safe traveling, switching from the autonomous driving mode to the manual driving mode is executed only in a case where it can be observed that the driver is in an internal return state.

4. Example of Monitoring

Therefore, an example of monitoring (observation) of switching from the autonomous driving mode to the manual driving mode will be described with reference to FIG. 4. FIG. 4 is a flowchart illustrating an example of a monitoring operation according to the embodiment of the present disclosure. As illustrated in FIG. 4, in the embodiment of the present disclosure, for example, in switching from the autonomous driving mode to the manual driving mode, the vehicle control system executes steps from step S21 to step S27. Details of each of these steps will be described below.

First, it is assumed that a vehicle travels in the autonomous driving mode and a driver is completely separated from a driving steering. Moreover, it is assumed that the driver is executing a secondary task such as a nap, watching videos, a game play in deep concentration, or work using a visual tool such as a tablet or a smartphone. On the other hand, it is assumed that work using a visual tool such as a tablet or a smartphone is performed, for example, in a state in which the driver's seat is reclined or in a seat different from the driver's seat.

First, the vehicle control system intermittently executes passive monitoring and/or active monitoring of the driver as appropriate (step S21). Here, active monitoring and passive monitoring will be described.

First, active monitoring is an observation method in which a vehicle control system inputs active information to a driver and observes a conscious response of the driver in response to the active information in order to mainly determine intellectual abilities of the driver such as a perception ability, a cognition ability, a determination ability, and an action ability. For example, examples of the active information input to the driver include visual information, auditory information, tactile information, olfactory information, and (taste) information. These pieces of active information cause a perceptive and cognitive action of the driver. In a case where the active information is information affecting a risk, the driver will perform (respond to) a determination or an action according to the risk. Thus, by observing such a driver's response, it is possible to determine a perception state, a cognition state, a determination state, and an action state of a brain of the driver. Specifically, in active monitoring, for example, in a case where the vehicle control system executes a steering control with a slight steering amount that does not affect safe traveling of the vehicle and corresponds to pseudo active information in order to prompt a feedback of the driver, an action of the driver to return the steering with an appropriate steering amount is expected (in a case where the driver is normally awakening) as a conscious response (in detail, the driver performs a series of actions of perceiving and recognizing an unnecessary steering amount, making a determination to return the steering with respect to the unnecessary steering amount, and taking an action, and thus an action corresponding to the above-described response is induced. Therefore, by observing the above-described response, it is possible to determine a perception state, a cognition state, a determination state, and an action state of a brain of the driver). Note that, during a period for which the vehicle travels in the manual driving mode, since the driver constantly performs a series of operations of a perception, a cognition, a determination, and an action for a road environment and the like in order to execute steering, the vehicle control system can observe a conscious response of the driver without directly inputting active information to the driver (that is, it can be said that there is a response of driving steering). Moreover, in a case where the above-described active information input is repeatedly performed, these pieces of information are intelligently filtered in the brain of the driver and are treated as unnecessary (that is, "habituation"). Therefore, in the embodiment of the present disclosure, the frequency of the active information input is preferably set to an appropriate frequency in order to avoid the above-described "habituation".

Next, the passive monitoring is executed in a case where a conscious response of the driver in response to the direct active information input cannot be observed (active monitoring) or the like. There are various observation methods for the passive monitoring of a state of a driver, and for example, observation of biometric information of a driver may be used. More specifically, for example, in the passive monitoring, in a case where a driver seats on the driver's seat and is in a posture that allows driving, it is expected to perform detailed observation evaluation of an eye opening ratio (PERCLOS) related index, a head posture behavior, an eyeball behavior (saccade (rapid eye movement), fixation, microsaccade, and the like), blinking, a facial expression, a face direction, and the like. Moreover, in a posture other than sitting, by using a wearable device or the like, it is possible to perform extended observation for observing a heart rate, a pulse rate, a blood flow, respiration, an electroencephalogram, a sweating state, a drowsiness level estimated from the heart rate and the respiration, and the like. Moreover, in the passive monitoring, seating or leaving of a driver on the driver's seat, a movement, a movement destination, a posture, and the like of the driver may be observed. Moreover, a steering amount associated with an attention driving state of a driver (a state in which the manual driving is performed while maintaining appropriate attention for driving) may be directly observed. Furthermore, the information observed by the passive monitoring can be used to estimate a time required for the driver to return to the manual driving in a case where the driving control system issues a driving mode switching notification, a warning, or the like during a period for which the vehicle travels in the autonomous driving mode. Moreover, the information observed by the passive monitoring can be used to determine whether to perform switching to the emergency evacuation mode in a case where the driver does not want to return to the manual driving within a predetermined time.

Next, the description will be continued returning to FIG. 4. The vehicle control system notifies the driver of an RTI as a request for a return to the manual driving (step S22). At this time, for example, the driver is notified of the RTI as a request for a return to the manual driving using dynamic haptics such as vibration, or in a visual or auditory manner. Then, in response to such a notification of the RTI as a request for a return, the driver returns to the driver's seat in a normal awakening state, and returns to a high awakening state in which the driver can drive the vehicle under a normal consciousness. Note that the RTI as a return request may be performed a plurality of times in stages. In this case, the RTI as a return request may be performed by different means in each stage, and may be dynamically changed according to, for example, a state of the driver.

Next, the vehicle control system monitors a seating state, a seating posture, and the like of the driver (step S23). Moreover, the vehicle control system intensively executes active monitoring of the driver who is properly sitting on the driver's seat (step S24). For example, in order to prompt the driver to return to a high awakening state in which the driver can drive the vehicle under normal consciousness, the active monitoring includes performing active information input such as performing warning or the like to the driver, inputting pseudo noise steering to the manual steering control of the vehicle in a pseudo manner, or the like.

Next, the vehicle control system intensively monitors a face of the driver and an eyeball behavior such as saccade (eyeball behavior intensive monitoring) (step S25).

Here, monitoring of the eyeball behavior will be described. Although information related to a state of the driver can be observed by various means, it is difficult to directly observe a cognition, a determination, and an action in a brain of the driver. For example, in a case of using a functional magnetic resonance imaging (fMRI), an electroencephalogram (EEG), or the like, it is required to restrain a subject (driver). For this reason, the method is not suitable as means for observing a state of the driver in the embodiment of the present disclosure. Therefore, in the embodiment of the present disclosure, means for observing an eyeball behavior of the driver is used as one of various biometric information observation means. For example, in a case where the driver is sitting on the driver's seat, the eyeball behavior observation can be executed without specially restraining the driver. That is, it can be said that the eyeball behavior observation is a non-invasive and non-wearable observation means.

Furthermore, the eyeball behavior is a part of behaviors appearing by a biological reflex, and occurs in a case where a reaction that appears by adjusting an adaptive response with respect to a loop in which a response to an event change does not include a thought factor and a behavior that is not a reflexive response and is used for characteristic tracking so as to recognize a characteristic of a visual object and promote understanding of the characteristic are developed by a fixation, the reaction including a smooth pursuit for relatively chasing a visual moving object (a sliding tracking eyeball movement), a slow congestion occurred due to an approach of a vehicle to a forward background and a high-speed return improvement movement for solving the congestion, a sliding tracking eyeball movement for tracking an object in a target direction regardless of rotations of a body and a head of a driver, and the like, and the behavior including a characteristic microsaccade and the like. In these behaviors, many phenomena appeared by reflecting neural transmission and processing in a brain are also seen simultaneously. That is, it is considered that an activity result such as recognition of a fixation target, which is obtained by referring to a memory of the brain, is reflected. Therefore, by using a fact that a cognitive function activity in the brain is reflected in the eyeball behavior, it is possible to estimate an awakening level of the driver with high accuracy on the basis of analysis of the eyeball behavior. That is, by executing the eyeball behavior observation, when performing switching from the autonomous driving mode to the manual driving mode (in detail, immediately before switching), it is possible to indirectly observe whether or not the driver returns to a high awakening level at which the driver can drive the vehicle under normal consciousness (return correspondence level). In particular, in a case where the driver once leaves the driving steering work and returns to the driving steering work after a lapse of time, it is considered that the driver does not have sufficient memories related to surroundings and a vehicle state required for returning to the manual driving. Therefore, for example, the driver tries to quickly perform an action for grasping information that the driver would have grasped in a case where the driver is performing continuous manual driving, such as visually checking a situation in front of the road or visually checking a cause of the RTI as a request for a return to the manual driving from the vehicle control system. Such an action for grasping information is reflected in the eyeball behavior of the driver.

Moreover, as described above, the eyeball behavior indicates a specific behavior for each person and further for each state of the person. Thus, in a case where it is desired to accurately determine the awakening level of the driver by analyzing the eyeball behavior, it is required to constantly recognize and learn the eyeball behavior specified for each driver and determine the awakening level of the driver on the basis of such learning. Moreover, what the driver intensively checks and in what priority order the driver checks when the drivers returns to the manual driving are greatly affected by memories based on the driver's past risk experience and the like, and thus, change due to various factors such as a road situation and a traveling speed during traveling. Therefore, the eyeball behavior not only exhibits a behavior specified for each person but also changes by being affected by memories based on various experiences of the driver. In the present embodiment, an awakening level determination is not performed using a uniform determination for drivers, but a return ability determination of the same driver is performed on the basis of learning obtained by intermittent learning in an active observation section. Therefore, it is possible to more suitably perform a return ability determination for each driver.

Then, the vehicle control system determines the return correspondence level of the driver by determining the awakening level of the driver on the basis of the monitoring in step S25 described above (step S26). Then, the vehicle control system determines whether or not the driver is at a return reaction level at which the driver can cope with returning to the manual driving. The vehicle control system according to the present embodiment observes a return process of the driver in stages, and observes a response of the driver in each stage of the return process. Therefore, it is possible to perform complex determination. Then, the vehicle control system executes switching from the autonomous driving mode to the manual driving mode in a case where it is determined that the return to the manual driving is allowed with a predetermined accuracy on the basis of an internal awakening return of the driver and a check as to whether the driver can perform a manual driving action (step S27).

Note that the steps in FIG. 4 do not necessarily have to be performed in the described order, may be performed in an appropriately changed order, or may be partially performed in parallel. For example, the active monitoring in step S24 and the eyeball behavior intensive monitoring in step S25 may be performed in parallel, or may be performed in an order different from the order illustrated in FIG. 4.

5. Background Leading to Creation of Embodiments of Present Disclosure

Moreover, before describing details of the embodiment of the present disclosure, a background leading to a creation of the embodiment of the present disclosure by the present inventors will be described.

Meanwhile, there is a plurality of return processes and stages during a period for which the driver returns to the driver's seat from a nap state or an absence state and actually holds the steering wheel to mainly perform the manual driving, and ideally, the return correspondence level (awakening level) of the driver is increased every stage. Then, in the vehicle control system, even in a situation where the return correspondence level of the driver is not ideally increased, it is possible to use check means for checking various internal awakening returns of the driver and abilities of manual driving actions of the driver according to the return process and stage. For example, in a case where the driver returns from a state where the drivers takes a nap at a nap place in the vehicle or the driver takes a nap after leaving the driver's seat, by detecting a change in posture for returning to the driver's seat from a nap posture, rising of a foot, a movement of the seat, or the like as a body motion as a response indicating a return from a sleep state, it is possible to check the internal awakening return of the driver and the ability of a manual driving action of the driver. Furthermore, in a case where the driver returns from a working state such as a state where the driver leaves the driver's seat for a TV conference or the like, by detecting seating of the driver on the driver's seat, a check response operation to the RTI as a return request from the vehicle control system in a state where the driver has left the driver's seat, a movement action for returning to the driver's seat, or the like, it is possible to check the internal awakening return of the driver and the ability of the manual driving action of the driver. Moreover, in a case where the driver has reached the vicinity of the driver's seat, by detecting a check operation of the forward road by the driver, a check operation for pointing and calling the forward road as necessary, a change to a driving posture at the driver's seat and a movement of a foot due to the change to a driving posture, a direction of a head or a face due to the forward road check operation, and the like, it is possible to check the internal awakening return of the driver and the ability of the manual driving action of the driver. Furthermore, by detecting a visual check by the driver to the RTI as a return request from the vehicle control system, a line-of-sight movement (eyeball behavior) for checking message content involved in the RTI as a return request or a full return completion time, and the like, it is possible to check the internal awakening return of the driver and the ability of the manual driving action of the driver. Moreover, by detecting a line-of-sight movement (eyeball behavior) for checking a situation around the vehicle by the driver when the manual driving is started, an operation to autonomous driving release switches, a stepwise input of a torque to the steering wheel, a pressing action on the brake pedal, a pressing action on the accelerator pedal, an acceleration instruction and a deceleration instruction, a correction operation with respect to a virtual noise related to a steering angle input from the vehicle control system, and the like, it is possible to check the internal awakening return of the driver and the ability of the manual driving action of the driver. That is, the vehicle control system is required to observe the return correspondence level in the return process of the driver in a stepwise and complex manner. Then, at a final stage of such stepwise and complex observation, as one means for estimating levels of a cognition, a determination, and an action in the brain of the driver, sampling and analysis of the eyeball behavior are performed at a high frame rate.

Specifically, in a stage before performing the manual driving, as one means for accurately determining the awakening level of the driver, it is required to observe an eyeball behavior in which an activity in the brain is reflected, particularly, a microsaccade. Therefore, in the following, a description will be given focusing on the eyeball behavior. As described above, the eyeball behavior indicates a behavior specified for each person. Therefore, in the vehicle control system, in order to accurately determine the awakening level of the driver using analysis of the eyeball behavior or the like, it is required not only to analyze the eyeball behavior in detail but also to constantly recognize and learn the eyeball behavior specified for each driver and determine the awakening level of the driver on the basis of such learning.

Therefore, in order to detect a superiority difference in the eyeball behavior of each driver, it is required to perform sampling and analysis of the eyeball behavior, which is a high-speed movement such as a microsaccade, at a high frame rate by an image capturing device or the like. However, in a case where such high-speed sampling and analysis are constantly performed, a load in imaging processing, analysis processing, and the like is increased. This leads to an increase in power consumption and an increase in device temperature. Moreover, in a situation where an amount of signals that can be acquired by executing high-speed sampling is decreased, a noise generated due to a temperature rise is increased. As a result, a detection sensitivity is decreased.

Specifically, in order to detect a superiority difference in the eyeball behavior of each driver, it is required to perform sampling and analysis of the high-speed movement of the eyeball of the driver at a high frame rate of, for example, 250 fps or higher, preferably, 1000 fps. Therefore, not only an increase in power consumption and transmission of large volumes of data are required, but also a signal is read at a high speed. Thereby, an integration time of an image signal can be shortened, and an amount of signals obtained by the integration can be reduced. Moreover, in a case where sampling and analysis are periodically performed at a high frame rate, a device temperature rises due to such an operation, and as a result, there is a side effect such as an increase in noise due to the temperature rise. For this reason, in general, it cannot be said that it is optimal to always perform sampling and analysis of the eyeball behavior at a high frame rate.

Furthermore, the detection sensitivity is decreased due to an increase in noise caused by the temperature rise. In order to compensate for the decrease in detection sensitivity, it is considered to increase light emission brightness of a light source. In this case, the light source with increased light emission brightness always lights the driver's eyes. However, for example, in a case where an infrared light source with increased light emission brightness continuously lights the driver's eyes, an exposure dose of the driver is increased, and this is not desirable from the viewpoint of driver's eye health.

Therefore, in view of such a situation, the present inventors have created an embodiment of the present disclosure for dynamically changing an operation of observing and analyzing the eyeball behavior, such as dividing the eyeball behavior of the driver into a period for sampling and analyzing the eyeball behavior at a high frame rate and other periods. According to the embodiment of the present disclosure, it is possible to accurately determine the awakening level (return correspondence level) of the driver while reducing a load in imaging processing, analysis processing, and the like. Thereby, according to the embodiment of the present disclosure, it is possible to reduce a load in imaging processing, analysis processing, and the like, and thus it is possible to avoid an increase in power consumption and an increase in device temperature. Further, it is possible to avoid a temperature rise, and thus the detection sensitivity is not reduced.

Specifically, during traveling in the autonomous driving mode, the driver does not perform manual driving. Thus, a period in which only passive monitoring is appropriately performed, and a period in which the eyeball behavior is observed and analyzed in order to determine the awakening level of the driver in a case where an event of switching from the autonomous driving mode to the manual driving mode occurs are included. That is, during traveling in the autonomous driving mode, sampling and analysis of the eyeball behavior may be executed at a high frame rate in a case where a switching event mainly occurs, and otherwise, it is not required to execute such sampling and analysis. Therefore, in the embodiment of the present disclosure, the operation of sampling and analyzing the eyeball behavior is dynamically changed such that sampling and analysis of the eyeball behavior are performed at a high frame rate in a case where an event of switching from the autonomous driving to the manual driving occurs, and otherwise, sampling and analysis of the eyeball behavior are performed at a low frame rate. As described above, in the present embodiment, sampling and analysis of the eyeball behavior are not always performed at a high frame rate. Thereby, it is possible to accurately determine the awakening level of the driver while reducing a load in imaging processing, analysis processing, and the like.

More specifically, in a period in which the switching event occurs (in detail, a switching preparation period), sampling and analysis of the eyeball behavior are performed at a high frame rate of, for example, 250 fps or higher, preferably, 1000 fps. Thereby, the awakening level of the driver is accurately determined. On the other hand, in other periods, sampling and analysis of the eyeball behavior are performed at a normal frame rate of, for example, 60 fps or the like. Thereby, a degree of fatigue and drowsiness of the driver are recognized (passive monitoring). Furthermore, at that time, it is possible to acquire a drowsiness evaluation value such as PERCLOS from blinking or a degree of eye opening. Furthermore, in the present embodiment, the vehicle control system may acquire not only the eyeball behavior but also various information such as information by the passive monitoring described above, information by the expression analysis, and a careless driving state, from a captured image of a face or a head of the driver at a normal frame rate, and determine the awakening level (return correspondence level) of the driver using such information.

Furthermore, in a case where sampling (imaging) of the eyeball behavior is performed at a high frame rate, a period in which signals can be integrated in each frame (each imaging period) is shortened. Thus, in order to integrate an amount of signals required for accurate analysis, during the imaging period, a light source with high light emission brightness lights the driver's eyes. In the present embodiment, in a case of lighting the driver's eyes with visible light during the manual driving, the driver's view is obstructed. Thus, lighting is performed with infrared light that does not affect the visibility of the retina. However, in a case where an infrared light source with increased light emission brightness continuously lights the driver's eyes, the infrared light imposes a burden on the retina even though the infrared light is invisible to the driver's eyes. Thus, excessive irradiation is not desirable from the viewpoint of driver's eye health. Therefore, according to the present embodiment, sampling of the eyeball behavior is performed at a high frame rate in a limited period. Thereby, the irradiation period by the light source with increased light emission brightness is limited, and thus a burden on the retina of the driver can be reduced.

Note that, in the example described in the present specification, a case where an image capturing device that performs sampling at a predetermined frame rate is used has been described. On the other hand, the present embodiment is not limited thereto. For example, in the present embodiment, in a case where a change in consecutively acquired captured images is recognized, observation may be performed using an event-driven imaging device that generates a signal. In this case, for example, a light emission timing of the light source that lights the face, the eyeball, or the like of the driver may be controlled using a signal generated due to an event detection by the event-driven imaging device, or the light emission timing and the imaging timing may be synchronized. For example, by using a signal by the event-driven imaging device as a trigger, sampling and analysis at a high frame rate in a predetermined period can be started, or irradiation of light with increased light emission brightness in a predetermined period can be started. Moreover, in change detection, an amount of a quantized difference may be controlled together. That is, by adjusting the light source and quantization control parameters to appropriately perform observation of the saccade and the microsaccade of the eyeball and using the event-driven imaging device, it is possible to efficiently perform a control such as dividing the eyeball behavior of the driver into a period for analyzing the eyeball behavior in a high sampling cycle and other periods.

Moreover, in a state where the awakening level of the driver is once lowered, the driver's attention to the surroundings is once lowered, and the attention to the surroundings is decreased. As a result, inactivation to a surrounding stimulus is progressed, and thus the eyeball behavior such as a microsaccade and a fixation tremor is reduced. Therefore, in the present embodiment, even in a period other than the period in which the event of switching the driving mode occurs, in a case where it is recognized that the awakening level of the driver is once lowered by passive monitoring, sampling and analysis of the eyeball behavior may be performed at a high frame rate according to such a state. The eyeball behavior observed at this time can be used for learning as training data associated with each driver and the awakening level of each driver. Then, in the present embodiment, in a period in which a switching event occurs, the awakening level (return reaction level) of the driver is determined with reference to the eyeball behavior that is specified for each driver and is obtained on the basis of such learning. Thus, it is possible to improve an accuracy of the determination. Even in such a case, in the present embodiment, sampling and analysis of the eyeball behavior are not always performed at a high frame rate. Thereby, it is possible to accurately determine the awakening level (return reaction level) of the driver while reducing a load in imaging processing, analysis processing, and the like. Hereinafter, details of the embodiment of the present disclosure created by the present inventors will be sequentially described.

6. Embodiment

6.1 Detailed Configuration of Vehicle Control System 100

First, a detailed configuration of the vehicle control system (information processing system) 100 according to the embodiment of the present disclosure will be described with reference to FIG. 5 and FIG. 6. FIG. 5 is an explanatory diagram illustrating an example of a detailed configuration of the vehicle control system 100 according to the present embodiment. Note that, in FIG. 6, in a case where a vehicle provided with the vehicle control system 100 is distinguished from other vehicles, the vehicle is hereinafter referred to as a host vehicle or an own vehicle.

As illustrated in FIG. 5, the vehicle control system 100 mainly includes an input unit 101, a data acquisition unit 102, a communication unit 103, an in-vehicle device 104, an output control unit 105, an output unit 106, a drive system control unit 107, a drive system 108, a body system control unit 109, a body system 110, a storage unit 111, an autonomous driving control unit 112, and a sensor unit 113. The input unit 101, the data acquisition unit 102, the communication unit 103, the output control unit 105, the drive system control unit 107, the body system control unit 109, the storage unit 111, and the autonomous driving control unit 112 are connected to each other via a communication network 121. The communication network 121 includes, for example, an in-vehicle communication network, a bus, or the like conforming to a certain standard, such as a controller area network (CAN), a local interconnect network (LIN), a local area network (LAN), or FlexRay (registered trademark). Note that the units of the vehicle control system 100 may be directly connected to each other without the communication network 121.

Note that, in the following description, a description of the communication network 121 will be omitted in a case where each unit of the vehicle control system 100 performs communication via the communication network 121. For example, in a case where the input unit 101 and the autonomous driving control unit 112 perform communication with each other via the communication network 121, it is simply described that the input unit 101 and the autonomous driving control unit 112 perform communication with each other.

Hereinafter, details of each functional unit included in the vehicle control system 100 according to the present embodiment will be sequentially described.

The input unit 101 includes a device used in a case where an occupant such as a driver inputs various data, instructions, and the like. For example, the input unit 101 includes operation devices such as a touch panel, a button, a microphone, a switch, and a lever, operation devices for which an input by a method other than a manual operation such as a voice or a gesture is allowed, and the like. Furthermore, for example, the input unit 101 may be a remote control device using infrared rays or other radio waves, or an external connection device such as a mobile device or a wearable device that responds to an operation of the vehicle control system 100. Then, the input unit 101 can generate an input signal on the basis of data, an instruction, or the like input by an occupant, and supply the input signal to each functional unit of the vehicle control system 100.

The data acquisition unit 102 can acquire data to be used for processing of the vehicle control system 100 from the sensor unit 113 including various sensors and the like, and supply the data to each functional unit of the vehicle control system 100.

For example, the sensor unit 113 includes various sensors for detecting a situation of the vehicle (host vehicle) and the like. Specifically, for example, the sensor unit 113 includes a gyro sensor, an acceleration sensor, an inertial measurement unit (IMU), and sensors for detecting an operation amount of an accelerator pedal, an operation amount of a brake pedal, a steering angle of a steering wheel, an engine rotation speed, a motor rotation speed, a rotation speed of a wheel, and the like.

Furthermore, for example, the sensor unit 113 may include various sensors for detecting information related to the outside of the vehicle (host vehicle). Specifically, for example, the sensor unit 113 may include an image capturing device such as a time-of-flight (ToF) camera, a stereo camera, a monocular camera, an infrared camera, or another camera. Furthermore, for example, the sensor unit 113 may include an environment sensor for detecting a weather, a condition, and the like, an ambient information detection sensor for detecting an object around the host vehicle, and the like. Examples of the environment sensor include a raindrop sensor, a fog sensor, a daylight sensor, and a snow sensor. Furthermore, examples of the ambient information detection sensor include an ultrasonic sensor, a radar, a LiDAR (light detection and ranging, laser imaging detection and ranging), a sonar, and the like.

Moreover, for example, the sensor unit 113 may include various sensors for detecting a current position of the vehicle (host vehicle). Specifically, for example, the sensor unit 113 may include a global navigation satellite system (GNSS) receiver or the like that receives a GNSS signal from a GNSS satellite.

Furthermore, for example, the sensor unit 113 may include various sensors for detecting information related to the inside of the vehicle. Specifically, for example, the sensor unit 113 may include an image capturing device that captures an image of the driver, a biometric information sensor that detects biometric information of the driver, a microphone that collects a sound in the inside of the vehicle, and the like. The biometric information sensor is provided, for example, on a seat surface of a seat, a steering wheel, or the like, and can detect biometric information of an occupant sitting on the seat or a driver gripping the steering wheel. Examples of the biometric information of the driver include a heart rate, a pulse rate, a blood flow, respiration, a brain wave, a skin temperature, a skin resistance, a sweating state, a head posture behavior, and an eyeball behavior (a gaze, a blink, a saccade, a microsaccade, a fixation, a drift, staring, a pupil response of an iris, and the like). These pieces of biometric information can be detected by using a potential between predetermined positions on a body surface of a driver or the like, a signal obtained by a contact observation such as a blood flow using infrared light, a non-contact microwave or millimeter wave, a signal obtained by a non-contact observation using a frequency modulation (FM) wave, detection of an eyeball behavior using a captured image of an eyeball by an image capturing device (monitoring unit) using an infrared wavelength, or overload torque measurement information of a steering or a pedal steering device for checking a steering response, individually or in combination.

The communication unit 103 performs communication with the in-vehicle device 104, various devices outside the vehicle, a server, a base station, and the like, and can transmit data supplied from each functional unit of the vehicle control system 100 and supply received data to each functional unit of the vehicle control system 100. Note that, in the embodiment of the present disclosure, a communication protocol supported by the communication unit 103 is not particularly limited and the communication unit 103 can support a plurality of types of communication protocols.

For example, the communication unit 103 can perform wireless communication with the in-vehicle device 104 by wireless LAN, Bluetooth (registered trademark), near field communication (NFC), wireless universal serial bus (WUSB), or the like. Furthermore, for example, the communication unit 103 can perform wired communication with the in-vehicle device 104 by USB, high-definition multimedia interface (HDMI) (registered trademark), mobile high-definition link (MHL), or the like via a connection terminal (not illustrated) (including a cable as necessary).

Moreover, for example, the communication unit 103 can perform communication with a device (for example, an application server or a control server) existing on an external network (for example, the Internet, a cloud network, or a specific network provided by a company) via a base station or an access point. Furthermore, for example, the communication unit 103 can perform communication with a terminal (for example, a terminal of a pedestrian or a store, or a machine type communication (MTC) terminal) existing in the vicinity of the host vehicle using a peer-to-peer (P2P) technique. Moreover, for example, the communication unit 103 may perform V2X communication such as vehicle-to-vehicle communication, vehicle-to-infrastructure communication, vehicle-to-home communication, or vehicle-to-pedestrian communication. Furthermore, for example, the communication unit 103 may include a beacon receiving unit, receive a radio wave or an electromagnetic wave transmitted from a wireless station or the like provided on a road, and acquire information such as a current position, congestion, traffic restrictions, a required time, or the like. Note that the communication unit 103 may be used in a complementary manner by performing pairing with a forward traveling vehicle that travels in a section and is a preceding vehicle, acquiring, as pre-traveling information, information acquired from a data acquisition unit provided in the forward vehicle, and complementing data acquired by the data acquisition unit 102 of the host vehicle. In particular, note that the communication unit 103 can be means for further ensuring safety of the following vehicle following after the preceding vehicle.

The in-vehicle device 104 may include, for example, a mobile device or a wearable device possessed by an occupant, an information device carried in or attached to the host vehicle, a navigation device that searches for a route to a certain destination, and the like. Note that, considering that an occupant is not necessarily fixed at a seat-fixed position according to spreading of the autonomous driving, the in-vehicle device 104 can be expanded to a video player, a game device, or another device that is provided in a vehicle and can be detachably used from the vehicle.

The output control unit 105 can control output of various information to an occupant of the host vehicle or the outside of the vehicle. For example, the output control unit 105 controls output of visual information (for example, image data) and auditory information (for example, audio data) from the output unit 106 by generating an output signal including at least one of the visual information or the auditory information and supplying the output signal to the output unit 106. Specifically, for example, the output control unit 105 generates a bird's-eye image, a panoramic image, or the like by combining pieces of image data captured by different image capturing devices included in the sensor unit 113, and supplies an output signal including the generated image to the output unit 106. Note that, in a case where such a bird's-eye image, a panoramic image, or the like is generated, it is possible to more precisely reproduce an event by recording and storing images before combination processing by compound eye in an allowable use form. Furthermore, recording and storing of the images before combination processing depend on whether to store the information and a transmission load. Furthermore, for example, the output control unit 105 generates sound data including a warning sound, a warning message, or the like for dangers such as a collision, a contact, or an entry into a danger zone, and supplies an output signal including the generated sound data to the output unit 106.

The output unit 106 may include a device capable of outputting visual information or auditory information to an occupant of the host vehicle or the outside of the vehicle. For example, the output unit 106 includes a display device, an instrument panel, an audio speaker, a headphone, a wearable device such as a glasses-type display worn by an occupant, a projector, a lamp, and the like. The display device included in the output unit 106 may be a device that displays visual information in a field of view of the driver, such as a head-up display, a transmissive display, or a device having an augmented reality (AR) display function, in addition to a device including a normal display. Note that the output unit 106 may include various devices that provide an olfactory stimulus (providing a predetermined odor) or a tactile stimulus (providing cold air, providing vibration, providing an electrical stimulation, and the like) to the driver in order to prompt awakening of the driver in a case where a large deviation from driving steering work of the driver occurs due to sleep or the like. Moreover, the output unit 106 may include a device or the like that provides a physical discomfort stimulus, such as a device that forces the driver into a posture causing discomfort by moving a backrest of the driver's seat.

The drive system control unit 107 can control the drive system 108 by generating various control signals and supplying the control signals to the drive system 108. Furthermore, the drive system control unit 107 may supply a control signal to each functional unit other than the drive system 108 as necessary, and perform notification of a control status of the drive system 108 and the like.

The drive system 108 may include various devices related to the drive system of the host vehicle. For example, the drive system 108 includes a driving force generation device for generating a driving force, such as an internal combustion engine or a driving motor, a driving force transmission mechanism for transmitting the driving force to wheels, a steering mechanism for adjusting a steering angle, a braking device for generating a braking force, an antilock brake system (ABS), an electronic stability control (ESC), an electric power steering device, and the like.

The body system control unit 109 can control the body system 110 by generating various control signals and supplying the control signals to the body system 110. Furthermore, the body system control unit 109 may supply a control signal to each functional unit other than the body system 110 as necessary, and perform notification of a control status of the body system 110 and the like.

The body system 110 may include various devices of a body system provided on a vehicle body. For example, the body system 110 includes a keyless entry system, a smart key system, a power window device, a power seat, a steering wheel, an air conditioner, various lamps (for example, a head lamp, a back lamp, a brake lamp, a blinker, a fog lamp, and the like), and the like.

The storage unit 111 may include, for example, a read only memory (ROM), a random access memory (RAM), a magnetic storage device such as a hard disc drive (HDD), a semiconductor storage device, an optical storage device, a magneto-optical storage device, or the like. Furthermore, the storage unit 111 can store various programs, data, and the like to be used by each functional unit of the vehicle control system 100. For example, the storage unit 111 stores map data such as a three-dimensional high-precision map such as a dynamic map, a global map which has a precision lower than a precision of the high-precision map and covers a wide area, and a local map including ambient information of the host vehicle.

The autonomous driving control unit 112 can perform a control related to autonomous driving such as autonomous traveling or driving support. Specifically, for example, the autonomous driving control unit 112 performs a cooperative control for the purpose of realizing a function of an advanced driver assistance system (ADAS) including collision avoidance or impact relaxation of the host vehicle, follow-up traveling based on an inter-vehicle distance, vehicle speed maintenance traveling, a collision warning of the host vehicle, a lane deviation warning of the host vehicle, and the like. Furthermore, for example, the autonomous driving control unit 112 can perform a cooperative control for the purpose of autonomous driving or the like in which the vehicle autonomously travels without depending on an operation of the driver. Specifically, the autonomous driving control unit 112 includes a detection unit 131, a self-position estimation unit 132, a situation analysis unit 133, a planning unit 134, and an operation control unit 135.

The detection unit 131 can detect various information required for controlling the autonomous driving. The detection unit 131 includes an outer-vehicle information detection unit 141, an in-vehicle information detection unit 142, and a vehicle state detection unit 143.

The outer-vehicle information detection unit 141 can perform detection processing of information related to the outside of the host vehicle on the basis of data or signals from each unit of the vehicle control system 100. For example, the outer-vehicle information detection unit 141 performs detection processing, recognition processing, and tracking processing of an object around the host vehicle, and detection processing of a distance to the object. Examples of the object as a detection target include a vehicle, a person, an obstacle, a structure, a road, a traffic light, a traffic sign, a road sign, and the like.

Furthermore, for example, the outer-vehicle information detection unit 141 performs detection processing of an ambient environment of the host vehicle. The ambient environment as a detection target includes, for example, a weather, a temperature, humidity, brightness, a road surface situation, and the like. For example, the outer-vehicle information detection unit 141 supplies data indicating a result of the detection processing to the self-position estimation unit 132, the map analysis unit 151, the traffic rule recognition unit 152, and the situation recognition unit 153 of the situation analysis unit 133, the emergency avoidance unit 171 of the operation control unit 135, and the like.

Note that the information acquired by the outer-vehicle information detection unit 141 may be mainly supplied from the infrastructure in a case where the traveling section is a section in which the vehicle can mainly travel by the autonomous driving and the constantly-updated LDM is supplied from the infrastructure. In a case where there is a vehicle or a vehicle group traveling ahead in the corresponding section, the host vehicle may receive the constantly-updated information from the vehicle or the vehicle group in advance before entering the section, and may travel in the section. Furthermore, in a case where the latest LDM is not constantly updated from the infrastructure, for the purpose of obtaining road information from vehicles in divided platooning traveling and further ensuring safety, road environment information, which is information immediately before the host vehicle enters the corresponding section and is obtained from preceding vehicles entering the section, may be complementarily further used. Whether the section is a section in which the autonomous driving is allowed is often determined by the presence or absence of prior information provided from these infrastructures. The updated new LDM that is provided from the infrastructure and is used for determining allowance of the autonomous driving on the route is equivalent to providing an invisible trajectory as so-called "information". Note that, for the sake of convenience, the outer-vehicle information detection unit 141 is illustrated on a premise of being provided in the own vehicle. By using information regarded as the "information" by the preceding vehicle, it is possible to further improve predictability of danger or the like that may occur in traveling.

The in-vehicle information detection unit 142 can perform detection processing of information related to the inside of the host vehicle on the basis of data or signals from each functional unit of the vehicle control system 100. For example, the in-vehicle information detection unit 142 performs driver authentication processing and driver recognition processing, driver state detection processing, occupant detection processing, in-vehicle environment detection processing, and the like. A state of the driver as a detection target includes, for example, a physical condition, an awakening level, a concentration level, a fatigue level, a line-of-sight direction, a detailed eyeball behavior, and the like. The in-vehicle environment as a detection target includes, for example, a temperature, humidity, brightness, odor, and the like. The in-vehicle information detection unit 142 supplies data indicating a result of the detection processing to the situation recognition unit 153 of the situation analysis unit 133, the emergency avoidance unit 171 of the operation control unit 135, and the like. Note that, for example, in a case where the driver is notified of the RTI as a request for a return to the manual driving and then determines that the driver cannot achieve the manual driving within a predetermined deadline time and where the driver determines that a return to the manual driving cannot be performed in time even though a deceleration control is performed and time extension is performed, the in-vehicle information detection unit 142 may output an instruction to the emergency avoidance unit 171 or the like, and may start a vehicle evacuation process including deceleration, evacuation, and stop.

Moreover, as described above, since it is assumed that the driver completely leaves driving steering work and uses another work, the driver may temporarily doze off or start another work (secondary task). Thus, it is required to recognize a return degree of an awakening level of consciousness required for returning to driving. Therefore, the above-described in-vehicle information detection unit 142 mainly has two major roles including a first role and a second role, the first role being passive monitoring of a state of the driver during driving, and the second role being active monitoring for detecting and determining whether or not the driver is at a return reaction level at which the manual driving is allowed by a conscious response of the driver after a notification of the RTI as a request for a return to the manual driving is performed.

The vehicle state detection unit 143 can perform detection processing of a state of the vehicle (host vehicle) on the basis of data or signals from each unit of the vehicle control system 100. The state of the host vehicle as a detection target includes, for example, a speed, acceleration, a steering angle, presence and absence of abnormality and content of the abnormality, a state of a driving operation, a position and an inclination of a power seat, a state of door lock, a state of another in-vehicle device, and the like. The vehicle state detection unit 143 supplies data indicating a result of the detection processing to the situation recognition unit 153 of the situation analysis unit 133, the emergency avoidance unit 171 of the operation control unit 135, and the like.

Note that the state of the vehicle (host vehicle) as a recognition target may include, for example, a position, a posture, and a movement (for example, a speed, acceleration, a moving direction, and the like) of the vehicle (host vehicle), a cargo load capacity related to determination of motion characteristics of the vehicle (host vehicle) and a movement of a center of a vehicle body due to a cargo load, a tire pressure, a braking distance movement due to a wear situation of a braking pad for a brake, allowable maximum deceleration braking for preventing cargo movement caused by braking of a load, a centrifugal force relaxation limit speed in curve traveling according to a liquid load, and the like. Note that, in the present embodiment, a return start timing required for a control varies depending on specific characteristics of the vehicle even in an exactly-same road environment and further depending on a load and the like such as a specific condition of a loaded cargo, a friction coefficient of a road surface, and a curve and a gradient of a road. Therefore, it is required to collect and learn various conditions and reflect the conditions at an optimum timing for performing a control.

The self-position estimation unit 132 can perform estimation processing of a position, a posture, and the like of the vehicle (host vehicle) on the basis of data or signals from each functional unit of the vehicle control system 100 such as the outer-vehicle information detection unit 141 and the situation recognition unit 153 of the situation analysis unit 133. Furthermore, the self-position estimation unit 132 can generate a local map (hereinafter, referred to as a self-position estimation map) used for estimating a self-position as necessary.

The self-position estimation map is, for example, a high-precision map using a technique such as simultaneous localization and mapping (SLAM). The self-position estimation unit 132 supplies data indicating a result of the estimation processing to the map analysis unit 151, the traffic rule recognition unit 152, the situation recognition unit 153, and the like of the situation analysis unit 133. Furthermore, the self-position estimation unit 132 can also store the self-position estimation map in the storage unit 111.

The situation analysis unit 133 can perform analysis processing of a situation of the vehicle (host vehicle) and a situation around the vehicle. The situation analysis unit 133 includes a map analysis unit 151, a traffic rule recognition unit 152, a situation recognition unit 153, and a situation prediction unit 154.

The map analysis unit 151 can perform analysis processing of various maps stored in the storage unit 111 and configure a map including information required for autonomous driving processing, while using data or signals from each functional unit of the vehicle control system 100, such as the self-position estimation unit 132 and the outer-vehicle information detection unit 141 as necessary. The map analysis unit 151 supplies the configured map to the traffic rule recognition unit 152, the situation recognition unit 153, the situation prediction unit 154, and the route planning unit 161, the action planning unit 162, the operation planning unit 163, and the like of the planning unit 134.

The traffic rule recognition unit 152 can perform recognition processing of traffic rules around the vehicle (host vehicle) on the basis of data or signals from each unit of the vehicle control system 100, such as the self-position estimation unit 132, the outer-vehicle information detection unit 141, and the map analysis unit 151. By this recognition processing, for example, a position and a situation of a traffic signal around the vehicle (host vehicle), content of traffic rules around the host vehicle, a lane on which the host vehicle can travel, and the like are recognized. The traffic rule recognition unit 152 supplies data indicating a result of the recognition processing to the situation prediction unit 154 and the like.

The situation recognition unit 153 can perform recognition processing of a situation of the vehicle (host vehicle) on the basis of data or signals from each functional unit of the vehicle control system 100, such as the self-position estimation unit 132, the outer-vehicle information detection unit 141, the in-vehicle information detection unit 142, the vehicle state detection unit 143, and the map analysis unit 151. For example, the situation recognition unit 153 performs recognition processing of a situation of the vehicle (host vehicle), a situation around the vehicle (host vehicle), a situation of a driver of the vehicle (host vehicle), and the like. Furthermore, the situation recognition unit 153 generates a local map (hereinafter, referred to as a situation recognition map) used to recognize a situation around the vehicle (host vehicle) as necessary. The situation recognition map is, for example, an occupancy grid map. Furthermore, the situation recognition unit 153 supplies data (including the situation recognition map as necessary) indicating a result of the recognition processing to the self-position estimation unit 132, the situation prediction unit 154, and the like. Furthermore, the situation recognition unit 153 stores the situation recognition map in the storage unit 111.

The situation prediction unit 154 can perform prediction processing of a situation of the vehicle (host vehicle) on the basis of data or signals from each unit of the vehicle control system 100, such as the map analysis unit 151, the traffic rule recognition unit 152, and the situation recognition unit 153. For example, the situation prediction unit 154 performs prediction processing of a situation of the vehicle (host vehicle), a situation around the vehicle (host vehicle), a situation of the driver, and the like. Note that the situation of the vehicle (host vehicle) as a prediction target includes, for example, a behavior of the vehicle (host vehicle), an occurrence of abnormality, a travelable distance, and the like. The situation around the vehicle (host vehicle) as a prediction target includes, for example, a behavior of a moving object around the vehicle (host vehicle), a change in a traffic signal state, a change in an environment such as weather, and the like. The situation of the driver as a prediction target includes, for example, a behavior and a physical condition of the driver. Then, the situation prediction unit 154 supplies data indicating a result of the prediction processing together with the data from the traffic rule recognition unit 152 and the situation recognition unit 153, to the route planning unit 161, the action planning unit 162, the operation planning unit 163, and the like of the planning unit 134.

The route planning unit 161 can plan a route to a destination on the basis of data or signals from each functional unit of the vehicle control system 100, such as the map analysis unit 151 and the situation prediction unit 154. For example, the route planning unit 161 sets a route from a current position to a designated destination on the basis of the global map. Furthermore, the route planning unit 161 sets an autonomous driving level for each section on the traveling route on the basis of the LDM and the like. Furthermore, for example, the route planning unit 161 may appropriately change the route on the basis of a situation such as a traffic jam, an accident, a traffic restriction, and a construction, a physical condition of the driver, and the like. The route planning unit 161 supplies data indicating the planned route to the action planning unit 162 and the like.

The action planning unit 162 can plan an action of the vehicle (host vehicle) for safe traveling on the route planned by the route planning unit 161 within a planned time on the basis of data or signals from each functional unit of the vehicle control system 100, such as the map analysis unit 151 and the situation prediction unit 154. For example, the action planning unit 162 performs planning of a start, a stop, a traveling direction (for example, forward movement, backward movement, left turn, right turn, direction change, and the like), a traveling lane, a traveling speed, overtaking, and the like. The action planning unit 162 supplies data indicating the planned action of the vehicle (host vehicle) to the operation planning unit 163 and the like.

The operation planning unit 163 can plan an operation of the vehicle (host vehicle) for realizing the action planned by the action planning unit 162 on the basis of data or signals from each functional unit of the vehicle control system 100, such as the map analysis unit 151 and the situation prediction unit 154. For example, the operation planning unit 163 performs planning of acceleration, deceleration, a traveling trajectory, and the like. Furthermore, the operation planning unit 163 can plan setting of a driving mode, a timing for executing switching, and the like. The operation planning unit 163 supplies data indicating the planned operation of the vehicle (host vehicle) to the acceleration/deceleration control unit 172, the direction control unit 173, and the like of the operation control unit 135.

The operation control unit 135 can control an operation of the vehicle (host vehicle). The operation control unit 135 includes an emergency avoidance unit 171, an acceleration/deceleration control unit 172, and a direction control unit 173.

The emergency avoidance unit 171 can perform processing of detecting an emergency such as a collision, a contact, an entry into a danger zone, abnormality of the driver, abnormality of the vehicle, or the like on the basis of detection results of the outer-vehicle information detection unit 141, the in-vehicle information detection unit 142, and the vehicle state detection unit 143. In a case where an occurrence of an emergency is detected, the emergency avoidance unit 171 plans an operation of the vehicle for avoiding the emergency, such as a sudden stop or a sudden turn. The emergency avoidance unit 171 supplies data indicating the planned operation of the vehicle to the acceleration/deceleration control unit 172, the direction control unit 173, and the like.

The acceleration/deceleration control unit 172 can perform acceleration/deceleration control for realizing the operation of the vehicle (host vehicle) that is planned by the operation planning unit 163 or the emergency avoidance unit 171. For example, the acceleration/deceleration control unit 172 calculates a control target value of the driving force generation device or the braking device for realizing the planned acceleration, deceleration, or sudden stop, and supplies a control command indicating the calculated control target value to the drive system control unit 107. Note that, for example, there are mainly two cases in which an emergency situation may occur. That is, there are a case where an unexpected accident occurs due to a sudden reason during autonomous driving on a road on which a traveling route in the autonomous driving mode is originally considered as being safe by LDM or the like acquired from the infrastructure and an emergency return of the driver cannot be performed in time, and a case where it is difficult to perform switching from the autonomous driving mode to the manual driving mode.

The direction control unit 173 can perform a direction control for realizing the operation of the vehicle (host vehicle) that is planned by the operation planning unit 163 or the emergency avoidance unit 171. For example, the direction control unit 173 calculates a control target value of the steering mechanism for realizing the traveling trajectory or the sudden turn that is planned by the operation planning unit 163 or the emergency avoidance unit 171, and supplies a control command indicating the calculated control target value to the drive system control unit 107.

Figure 6:
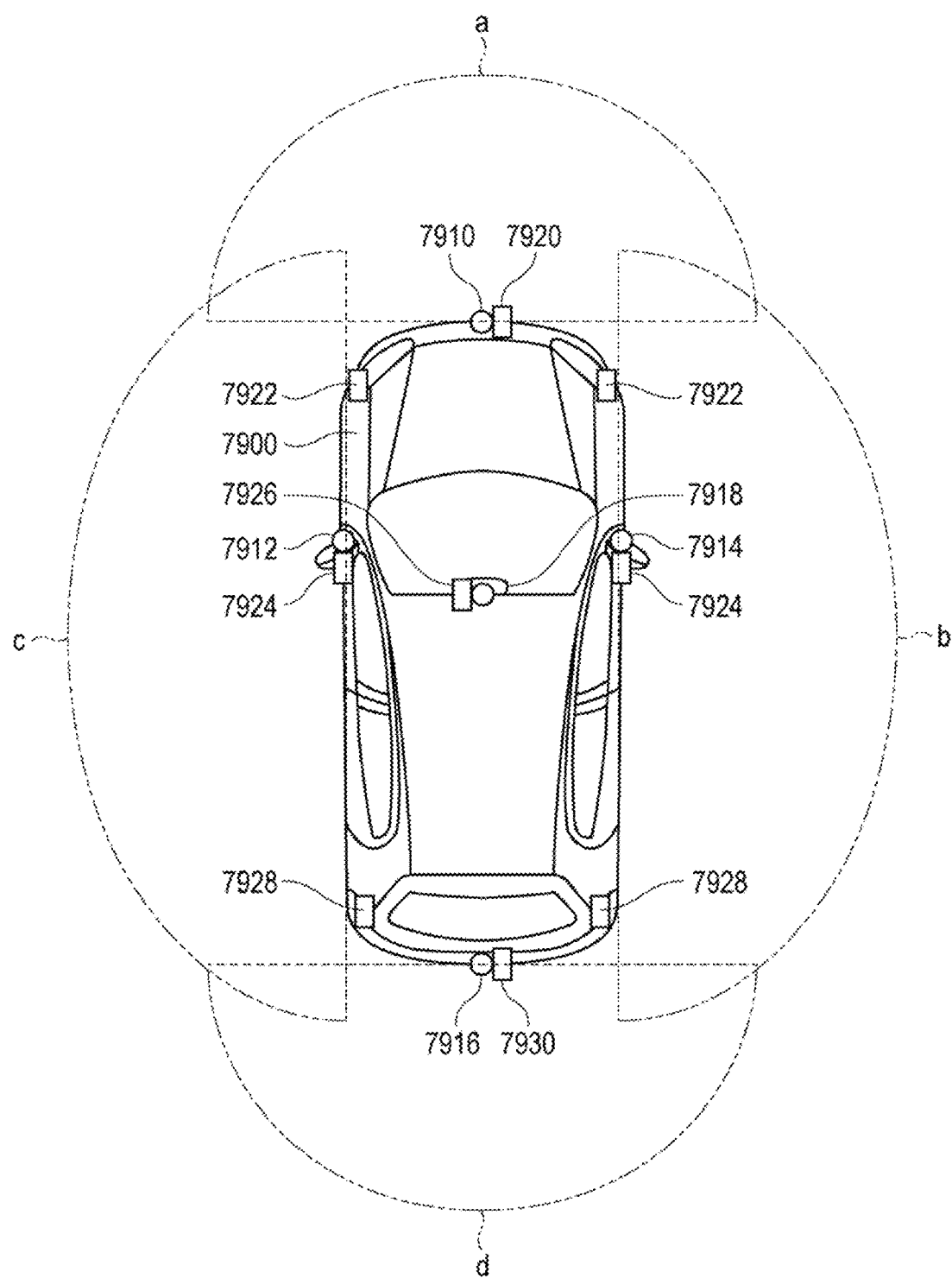
FIG. 6 is an explanatory diagram illustrating an example of an installation position of an image capturing device included in a sensor unit 113 according to the embodiment of the present disclosure.

Moreover, FIG. 6 is a diagram illustrating an example of an installation position of an image capturing device included in the sensor unit 113. As illustrated in FIG. 6, in a vehicle 7900, imaging units 7910, 7912, 7914, 7916, and 7918 to which image capturing devices can be respectively applied are installed, for example, at positions of at least one of a front nose, a side mirror, a rear bumper, a back door, or an upper portion of a windshield in the interior of the vehicle.

The imaging unit 7910 installed at the front nose and the imaging unit 7918 installed at the upper portion of the windshield in the interior of the vehicle mainly acquire images in front of the vehicle 7900. The imaging units 7912 and 7914 installed on the side mirrors mainly acquire images of sides of the vehicle 7900. The imaging unit 7916 installed on the rear bumper or the back door mainly acquires an image behind the vehicle 7900. The imaging unit 7918 installed on the upper portion of the windshield in the interior of the vehicle is mainly used to detect a preceding vehicle, a pedestrian, an obstacle, a traffic light, a traffic sign, a lane, or the like. Furthermore, in the future autonomous driving, in a case where the vehicle turns right or left, the imaging unit 7918 may be used to detect a pedestrian crossing a road at a right turn or a left turn in a wider range and an object approaching a crossing road in an expanded range.

Note that FIG. 6 illustrates an example of an imaging range of each of the imaging units 7910, 7912, 7914, and 7916. An imaging range a indicates an imaging range of the imaging unit 7910 installed at the front nose, imaging ranges b and c respectively indicate imaging ranges of the imaging units 7912 and 7914 installed at the side mirrors, and an imaging range d indicates an imaging range of the imaging unit 7916 installed at the rear bumper or the back door. For example, by superimposing image data captured by the imaging units 7910, 7912, 7914, and 7916, a bird's-eye image of the vehicle 7900 when viewed from above can be obtained. For example, by superimposing image data captured by the imaging units 7910, 7912, 7914, and 7916, a bird's-eye image of the vehicle 7900 when viewed from above, an omnidirectional stereoscopic display image in which portions around the vehicle are surrounded by a curved plane, or the like can be obtained.

The outer-vehicle information detection units 7920, 7922, 7924, 7926, 7928, and 7930 provided at a front, a rear, sides, corners, and an upper portion of a windshield in the interior of the vehicle 7900 may be, for example, ultrasonic sensors or radar devices. The outer-vehicle information detection units 7920, 7926, and 7930 provided at the front nose, the rear bumper, the back door, and the upper portion of the windshield in the interior of the vehicle 7900 may be, for example, LiDAR devices. These outer-vehicle information detection units 7920 to 7930 are mainly used to detect a preceding vehicle, a pedestrian, an obstacle, or the like. These detection results may be applied to improve display of a three-dimensional object such as bird's-eye display and omnidirectional stereoscopic display described above.

6.2 Detailed Configuration of Sensor Unit 113

Figure 7:
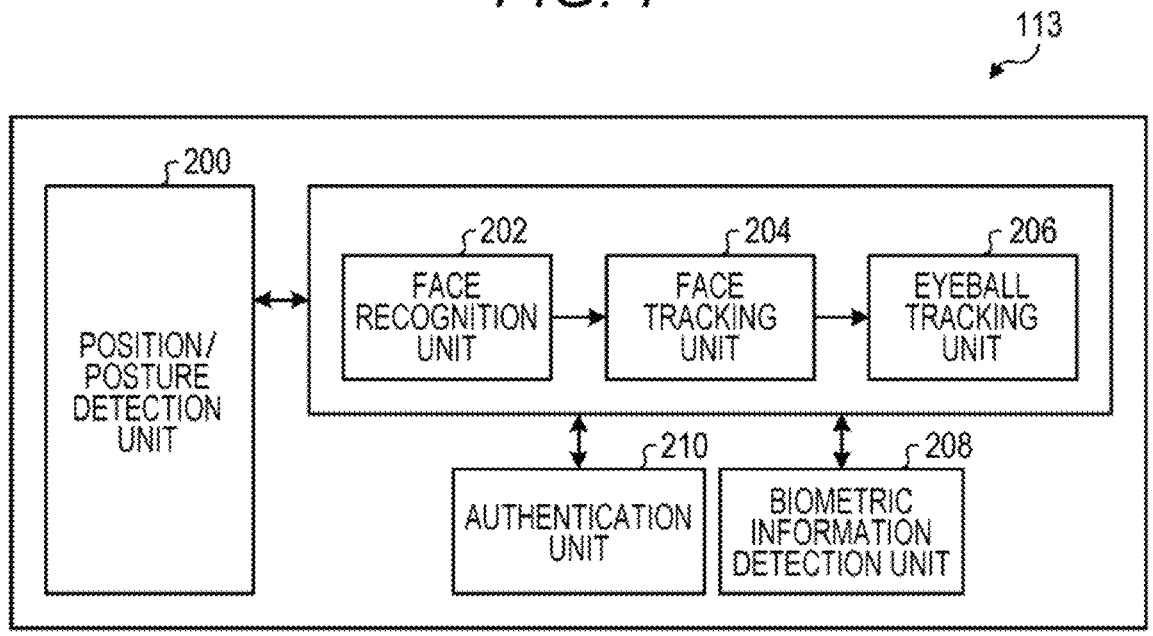
FIG. 7 is an explanatory diagram illustrating an example of various sensors included in the sensor unit 113 according to the embodiment of the present disclosure.

Next, an example of various sensors that are included in the sensor unit 113 described above and obtain information related to the driver in the vehicle will be described with reference to FIG. 7. FIG. 7 is an explanatory diagram illustrating an example of various sensors included in the sensor unit 113 according to the present embodiment. FIG. 7 is a diagram illustrating an example of various sensors that are included in the sensor unit 113 and obtain information related to the driver in the vehicle. As illustrated in FIG. 7, the sensor unit 113 includes a position/posture detection unit 200 that is a detector for detecting a position and a posture of the driver and includes, for example, a ToF camera, a stereo camera, a seat strain gauge, and the like. Furthermore, the sensor unit 113 includes a face recognition unit 202, a face tracking unit 204, and an eyeball tracking unit (monitoring unit) 206 that are detectors for obtaining biometric information of the driver. Hereinafter, details of various sensors included in the sensor unit 113 according to the present embodiment will be sequentially described.

The face recognition unit 202, the face tracking unit 204, and the eyeball tracking unit (monitoring unit) 206 may be configured with, for example, various sensors such as image capturing devices. For example, the face recognition unit 202 recognizes and detects a face of the driver or the like from the captured image, and outputs the detected information to the face tracking unit 204. The face tracking unit 204 detects a movement of a face or a head of the driver on the basis of the information detected by the face recognition unit 202. Moreover, the eyeball tracking unit 206 detects an eyeball behavior of the driver. Furthermore, the eyeball tracking unit 206 may include, for example, a sensor such as electro-oculogram (EOG) that measures a potential of an eyeball.

Moreover, the sensor unit 113 may include a biometric information detection unit 208 that is another detector for obtaining biometric information of the driver. Furthermore, the sensor unit 113 may include an authentication unit 210 that performs authentication of the driver. Note that, an authentication method of the authentication unit 210 may be biometric authentication using a face, a fingerprint, an iris of a pupil, a voiceprint, or the like in addition to knowledge authentication using a password, a personal identification number, or the like and is not particularly limited. In the above description, the main sensors included in the sensor unit 113 have been described. On the other hand, the sensor unit 113 may include various sensors other than the sensors.

Figure 8:
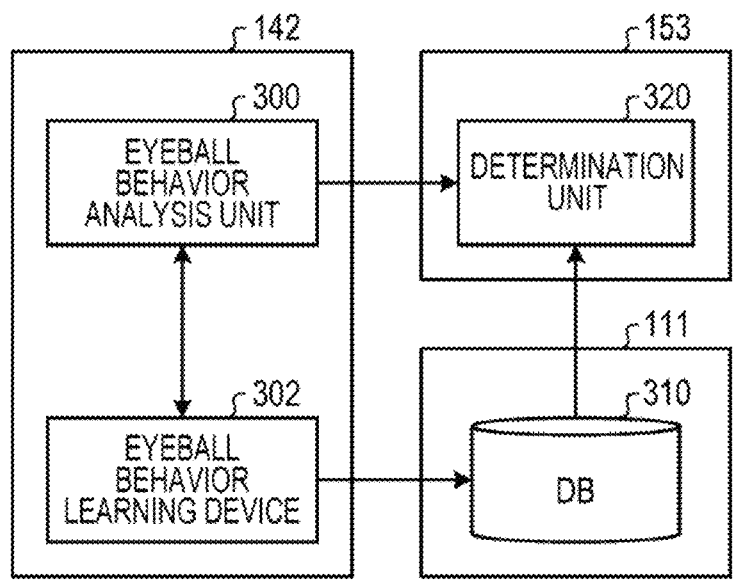
FIG. 8 is an explanatory diagram illustrating an example of a unit that executes determination of an awakening level of a driver according to the embodiment of the present disclosure.

6.3 Detailed Configuration of Unit for Executing Determination of Awakening Level of Driver Next, a specific configuration example of a unit that executes determination of an awakening level (return reaction level) of the driver according to the embodiment of the present disclosure will be described with reference to FIG. 8. FIG. 8 is an explanatory diagram illustrating an example of a unit that executes determination of the awakening level of the driver according to the present embodiment. Specifically, the unit that executes determination of the awakening level of the driver includes a part of the in-vehicle information detection unit 142 of the detection unit 131 illustrated in FIG. 5, the situation recognition unit 153 of the situation analysis unit 133, and the storage unit 111. More specifically, FIG. 8 illustrates an eyeball behavior analysis unit 300 and an eyeball behavior learning device 302 included in the in-vehicle information detection unit 142, a determination unit 320 included in the situation recognition unit 153, and a database (DB) 310 stored in the storage unit 111, and these units cooperate to determine the awakening level of the driver. Hereinafter, each functional block illustrated in FIG. 8 will be sequentially described.

(Eyeball Behavior Analysis Unit 300)

The eyeball behavior analysis unit 300 acquires and analyzes the eyeball behavior of the driver that is detected by the eyeball tracking unit 206 of the sensor unit 113 via the data acquisition unit 102. For example, the eyeball behavior analysis unit 300 detects and analyzes the eyeball behavior such as a saccade (rotation of an eyeball), a fixation, and a microsaccade (minute rotation of an eyeball) of the eyeball of the driver. The eyeball behavior information that is analyzed by the eyeball behavior analysis unit 300 is output to the eyeball behavior learning device 302 and the determination unit 320 to be described later.

Moreover, in the present embodiment, the eyeball behavior analysis unit 300 can perform dynamic switching of an analysis mode according to the driving mode or the like. For example, the eyeball behavior analysis unit 300 can perform switching between at least two analysis modes (first analysis mode and second analysis mode). Specifically, the eyeball behavior analysis unit 300 can perform analysis at a high frame rate (first frame rate) of, for example, 250 fps or higher in one analysis mode (first analysis mode), and can perform analysis at a low frame rate (second frame rate) of, for example, 60 fps in the other analysis mode (second analysis mode).

More specifically, in a case where an event in which the driving mode is switched from the autonomous driving mode to the manual driving mode occurs, the eyeball behavior analysis unit 300 intensively performs sampling and analysis of the eyeball behavior at a high frame rate in a period of a preparation mode for the switching (a period of a driving mode change preparation mode) (first analysis mode). In the eyeball behavior analysis, the eyeball behavior analysis unit 300 executes observation (sampling) and analysis of a microsaccade or a fixation tremor of the driver. Then, the determination unit 320 to be described later determines the awakening level (return reaction level) of the driver on the basis of the analysis result. Moreover, preferably, a time length of the period of the eyeball behavior analysis in the period of the preparation mode described above is determined such that a sufficient time is ensured to determine the awakening level (that is, the return correspondence level of the driver to the manual driving) of the driver with high accuracy before the vehicle reaches a switching point of the driving mode according to the autonomous driving level, the switching point being set on the route based on the LDM or the like. Therefore, in the present embodiment, a start point (monitoring point) of the period of the eyeball behavior analysis in the period of the preparation mode is determined on the basis of a schedule (course), the LDM, a road state, a traveling speed, a vehicle type (trailer or general passenger car), a seating state (state information) of the driver, and the like. That is, a time length of the period is dynamically changed.

Furthermore, in a case where the driving mode is the autonomous driving mode, the eyeball behavior analysis unit 300 performs sampling and analysis of the eyeball behavior at a low frame rate (second analysis mode). The eyeball behavior analysis is executed by the passive monitoring described above. For example, PERCLOS, a saccade, a fixation, and the like are also observed and analyzed to determine a drowsiness level or a fatigue level of the driver by the eyeball behavior analysis. Furthermore, in the case of the autonomous driving mode, the eyeball behavior analysis unit 300 may perform dynamic switching of an analysis frequency according to the autonomous driving level (the autonomous driving level 3 or the autonomous driving level 4). For example, in the autonomous driving level 3, the analysis may be executed at a higher frequency as compared with the analysis in the autonomous driving level 4. This is because, as described above, in the autonomous driving level 3, in order to ensure safe driving, it is expected that the driver is always in a preparation state such that the driver can immediately return to the manual driving. Therefore, in the autonomous driving level 3, it is preferable to execute eyeball behavior analysis at a high frequency in order to detect a drowsiness level and a fatigue level of the driver and determine whether or not the driver can immediately return to the manual driving.

On the other hand, in the above description, the specific autonomous driving levels such as the autonomous driving level 3 and the autonomous driving level 4 are distinguished and described. This is for the sake of convenience, and the actual operation is not necessarily limited to the example in which the autonomous driving levels are specifically distinguished and controlled. That is, since the autonomous driving level and the driving mode are changed according to a situation that changes from moment to moment, in order to determine whether or not the driver has a perception ability, a cognition ability, a determination ability, and an action ability required for returning to the manual driving, each device that observes the state of the driver, such as the eyeball behavior analysis unit 300, performs observation according to the situation as appropriate, and obtains observable evaluation values.

Moreover, even in a case of the autonomous driving mode, in order to acquire training data for learning by the eyeball behavior learning device 302 to be described later, for example, the eyeball behavior analysis unit 300 may execute eyeball behavior analysis at a high frame rate or a low frame rate in a period having a time length shorter than a time length of the period of the eyeball behavior analysis in the period of the preparation mode described above. For example, in a case where the driving mode is the autonomous driving mode and lowering of the awakening level of the driver is detected by the passive monitoring, the eyeball behavior analysis unit 300 may execute eyeball behavior analysis at a high frame rate (first analysis mode). The analysis result in this case is training data (training data which is labeled as the eyeball behavior when the awakening level is lowered) for learning by the eyeball behavior learning device 302 to be described later.

On the other hand, in a case where the driving mode is the manual driving mode, the eyeball behavior analysis unit 300 performs analysis of the eyeball behavior at a low frame rate (second analysis mode). The eyeball behavior analysis is executed by the passive monitoring described above. For example, PERCLOS, a saccade, a fixation, and the like are also observed and analyzed to determine a drowsiness level or a fatigue level of the driver by the eyeball behavior analysis. Then, even in a case of the manual driving mode, in a situation where it is checked that the driver performs manual driving in a normal state on the basis of a driving operation of the driver, in order to acquire training data (training data which is labeled as the eyeball behavior when the awakening level is normal) for learning by the eyeball behavior learning device 302 to be described later, the eyeball behavior analysis unit 300 may execute eyeball behavior analysis. In order to acquire the training data, for example, the eyeball behavior analysis unit 300 executes eyeball behavior analysis at a high frame rate or a low frame rate in a period having a time length shorter than a time length of the period of the eyeball behavior analysis in the period of the preparation mode described above. Furthermore, even in a case where the driving mode is the manual driving mode and lowering of the awakening level of the driver is detected by the passive monitoring, the eyeball behavior analysis unit 300 may execute eyeball behavior analysis at a high frame rate (first analysis mode). The analysis result in this case is also training data (training data which is labeled as the eyeball behavior when the awakening level is lowered) for learning by the eyeball behavior learning device 302 to be described later.

That is, in the present embodiment, the eyeball behavior analysis unit 300 does not always execute eyeball behavior analysis at a high frame rate. Thus, it is possible to reduce a load in imaging processing, analysis processing, and the like. Moreover, in the present embodiment, the eyeball behavior analysis unit 300 executes eyeball behavior analysis at a high frame rate as necessary. Thus, it is possible to accurately determine the awakening level (return reaction level) of the driver.

(Eyeball Behavior Learning Device 302)

The eyeball behavior learning device 302 learns, as training data, the analysis result of the eyeball behavior of the driver that is labeled with each awakening level and is acquired in the past, generates a database 310 for determination by the determination unit 320 to be described later, and outputs the database to the storage unit 111 (refer to FIG. 5). In the present embodiment, for example, the eyeball behavior learning device 302 may be a supervised learning device such as a support vector regression or a deep neural network. In this case, the analysis result (eyeball behavior) and the awakening level labeled with the analysis result (when the awakening level is normal or lowered) are respectively input to the eyeball behavior learning device 302, as an input signal and a training signal, and the eyeball behavior learning device 302 performs machine learning of a relationship between these pieces of input information according to a predetermined rule. Then, the eyeball behavior learning device 302 generates the database (DB) 310 that stores relationship information indicating a relationship between the analysis result (eyeball behavior) and the awakening level by receiving, as inputs, a plurality of pairs of the input signals and the training signals and performing machine learning of these inputs. Note that the generated DB 310 is not limited to as being stored in the storage unit 111 and may be stored in a server (not illustrated) on a cloud in association with identification information for identifying the driver. The stored DB 310 can also be used in different vehicles in a case where the driver transfers a commercial vehicle or uses a shared car or rental car. Moreover, it is preferable that the information in the DB 310 is always updated regardless of where the information is stored. Note that, in a case where a return requirement obtained by motion characteristics or the like varies depending on the type of the vehicle, normalization of an evaluation determination criterion according to the vehicle may be further performed.

(Determination Unit 320)

The determination unit 320 determines the awakening level (return reaction level) of the driver on the basis of the analysis result of the eyeball behavior that is analyzed by the eyeball behavior analysis unit 300. For example, in a case where it is checked that the driver executes an eyeball behavior such as a saccade, a fixation, or a microsaccade of an eyeball so as to solve a problem, the determination unit 320 can determine that the awakening level of the driver is high. On the other hand, in a case where these eyeball behaviors are not observed or are small, the determination unit 320 can determine that the awakening level of the driver is low.

Specifically, the eyeball behaviors indicate different behaviors in a case where a person is in a normal awakening state and a case where a person is in a state where consciousness or awakening is lowered. Moreover, each person exhibits a characteristic eyeball behavior. Therefore, in the present embodiment, the determination unit 320 performs a determination with reference to the database (DB) 310 generated by the eyeball behavior learning device 302 in association with each individual driver. More specifically, in the present embodiment, the determination unit 320 determines the awakening level (return correspondence level) by comparing the analysis result of the eyeball behavior of the driver in the period of the preparation mode with the database (DB) 310 based on the analysis result of the eyeball behavior of the driver that is acquired in the past. Therefore, in the present embodiment, the determination is performed with reference to the eyeball behavior that is obtained by learning and is specified for each driver. Thus, it is possible to improve an accuracy of the determination.

Moreover, the determination unit 320 can output the determination result to the situation prediction unit 154 (refer to FIG. 5) and the planning unit (moving object driving control unit) 134 (refer to FIG. 5). For example, the planning unit 134 may perform planning for switching of the driving mode on the basis of the determination result by the determination unit 320.

6.4 Operation Example of Eyeball Behavior Analysis Unit 300

Figure 9:
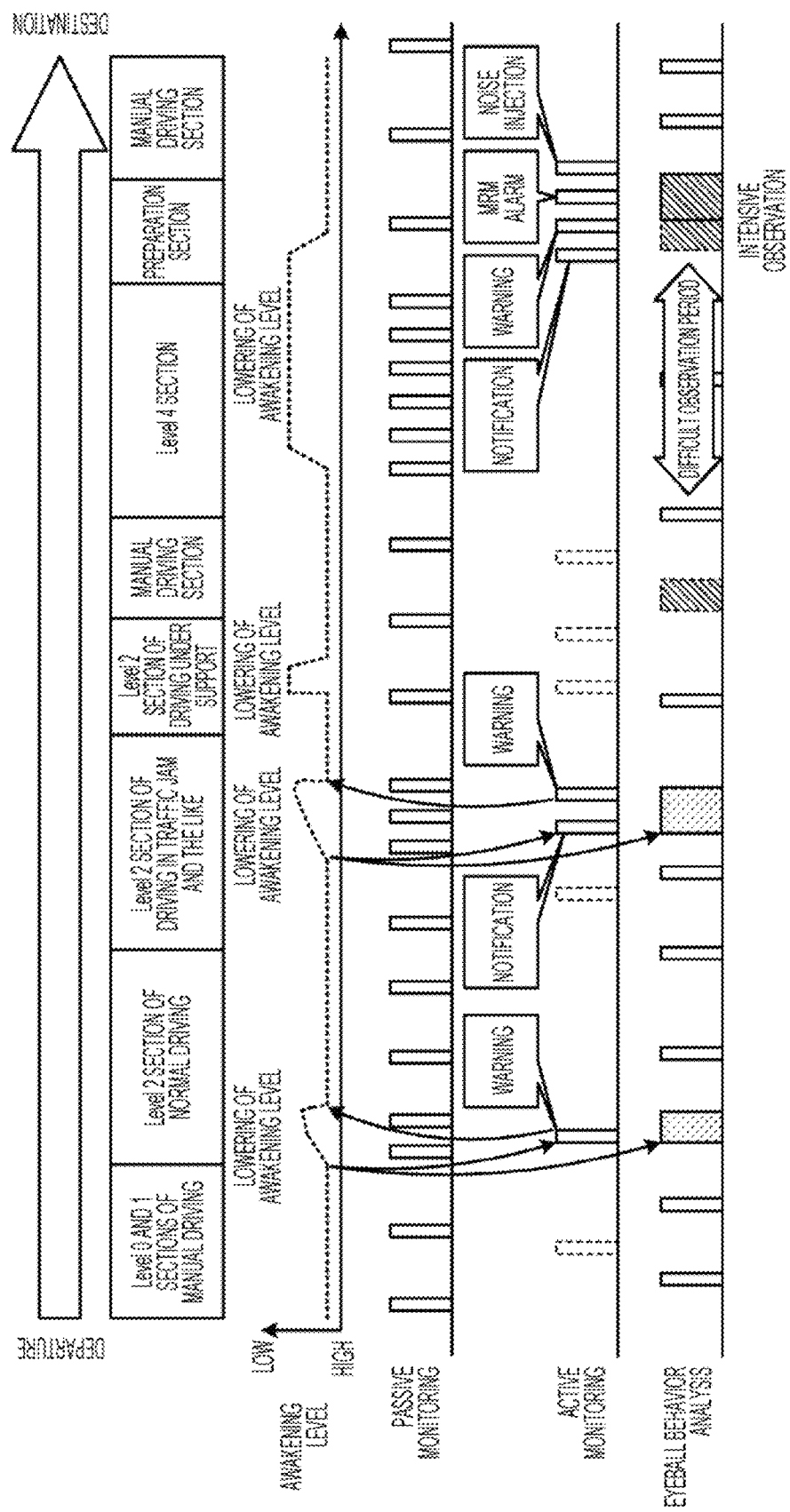
FIG. 9 is an explanatory diagram illustrating details of an operation example of an eyeball behavior analysis unit 300 according to the embodiment of the present disclosure.

Next, details of an operation example of the eyeball behavior analysis unit 300 according to the embodiment of the present disclosure will be further described with reference to FIG. 9. FIG. 9 is an explanatory diagram illustrating details of an operation example of the eyeball behavior analysis unit 300 according to the embodiment of the present disclosure. Note that, in FIG. 9, it is assumed that a left end is a departure point (departure) and a right end is a destination point (destination). In the following, a description will be given from the departure point to the destination point.

First, in the present embodiment, as illustrated in FIG. 9, passive monitoring is intermittently executed at a predetermined frequency regardless of the driving mode. For example, the passive monitoring includes eyeball behavior analysis at a low frame rate, and the eyeball behavior analysis is executed to observe and analyze, for example, PERCLOS, a saccade, a fixation, and the like and determine a drowsiness level and a fatigue level of the driver.

Furthermore, in the present embodiment, in a traveling section in the manual driving mode of the autonomous driving levels 0 and 1 illustrated on a left side of FIG. 9, not only the above-described passive monitoring is performed but also, in a situation where it is checked that the driver performs manual driving in a normal state on the basis of a driving operation of the driver, in order to acquire training data (training data which is labeled as the eyeball behavior when the awakening level is normal) for learning by the eyeball behavior learning device 302, eyeball behavior analysis (for example, a microsaccade) may be executed. In order to acquire the training data, for example, the eyeball behavior analysis unit 300 executes eyeball behavior analysis at a high frame rate.

Moreover, for example, in traveling sections in normal driving and a traffic jam and the like and in the manual driving mode of the autonomous driving level 2 illustrated on the left side of FIG. 9, it is assumed that lowering of the awakening level of the driver is detected by passive monitoring. In this case, passive monitoring may be performed more frequently, and eyeball behavior analysis (for example, a microsaccade) may be executed at a higher frame rate. The analysis result of the eyeball behavior in this case is training data (training data which is labeled as the eyeball behavior when the awakening level is lowered) for learning by the eyeball behavior learning device 302. Moreover, in response to detection of lowering of the awakening level of the driver, as active monitoring, a warning or a notification may be performed for the driver. In a case where the driver consciously responds to a warning or a notification, active monitoring can be executed. For example, as described above, in a case where the vehicle control system 100 executes a steering control with an unnecessary steering amount as active information, a notification is performed. In this case, an action of the driver to return the steering with an appropriate steering amount is a conscious response. Moreover, as indicated by a broken line of FIG. 9, active monitoring is not limited to as being executed in a case where the awakening level of the driver is lowered, and may be periodically performed at a predetermined frequency. On the other hand, in the manual driving mode, the driver constantly performs a road environment recognition determination for the manual driving. Thus, active monitoring as described above is not necessarily executed except in a situation where the awakening level of the driver is lowered.

Furthermore, in a section in the manual driving mode, eyeball behavior analysis may be periodically executed.

Then, in a traveling section in the autonomous driving mode of the autonomous driving level 4, the driver may leave the driver's seat. During this period, it is difficult to periodically execute eyeball behavior analysis (observation-disabled period). Therefore, during the period, passive monitoring may be performed with a higher frequency.

Next, in a section in the preparation mode for switching of the driving mode from the autonomous driving mode to the manual driving mode, eyeball behavior analysis is intensively executed at a high frame rate. Moreover, preferably, a time length of the period of the eyeball behavior analysis is determined such that a sufficient time is ensured to determine the awakening level of the driver with high accuracy before the vehicle reaches a switching point of the driving mode according to the autonomous driving level, the switching point being set on the route based on the LDM or the like. Therefore, in the present embodiment, a start point (monitoring point) of the period of the eyeball behavior analysis is determined on the basis of a schedule (course), the LDM, a road state, a traveling speed, a vehicle type (trailer or general passenger car), a seating state (state information) of the driver, and the like. That is, a time length of the period is dynamically changed. At this time, in a case where lowering of the awakening level of the driver is detected, an operation of returning the internal awakening of the driver is performed in an order of a notification, a warning, an MRM warning, noise injection (questions in a quiz form), and the like for the driver, and at the same time, active monitoring for detecting a conscious response of the driver is intensively executed.

That is, in the present embodiment, eyeball behavior analysis is not always executed at a high frame rate. Thus, it is possible to reduce a load in imaging processing, analysis processing, and the like. Moreover, in the present embodiment, eyeball behavior analysis is executed at a high frame rate as necessary. Thus, it is possible to accurately determine the awakening level (return reaction level) of the driver.

Note that the present applicant has already filed a plurality of patent applications (Patent Documents 2 to 4) for such a configuration for determining the return reaction level (awakening level) of the driver, specifically, a configuration related to observation for determination, and contents disclosed in these patent applications are also included in the embodiment of the present disclosure. Furthermore, the present applicant has already filed a patent application (refer to Patent Document 4) for a configuration for estimating a time required for the driver to appropriately return to the manual driving (manual driving return possible time) on the basis of a state evaluation value of the driver obtained by observation or the like before switching from the autonomous driving mode to the manual driving mode, and the configuration can also be used in the present embodiment.

In the present embodiment, various observations for the driver described in Patent Documents and the like are continuously performed, a tendency of the observation is learned, and the return reaction level such as the awakening level is determined in consideration of a change in the tendency at that time. This is because, even for the same driver, the driver's past experience and history affect a perception, a cognition, a determination, an action, and the like of the driver. Specifically, for example, the eyeball behavior to be observed greatly changes according to a method by which the driver feels a necessity of a return (switching) from the autonomous driving to the manual driving. For example, in a case where information required to reduce a risk by an intuitive action is insufficient, the number of times of search for information that can be visually acquired is increased. For this reason, in a case where information required for determination is sufficiently prepared, a shifting from a search to an action can be performed without searching for much information. Therefore, in a case where the information is insufficient, in order to search for insufficient information through recognition of individual visual information, the driver repeats an operation of fixing a line-of-sight of the driver toward a target, such as a fixation characterized with a saccade, a microsaccade, a drift, and a tremor.

In particular, at a stage of performing risk determination in a case where a return action from the autonomous driving to the manual driving is performed, pieces of information remaining in the memory have a high risk, and are insufficient for the determination. Thus, it is required for the driver to visually search for information. For example, in a case of the driver who has been watching a video or operating a mobile terminal or the like without looking forward for a while, the driver first checks the front of the vehicle for grasping the situation, and looks at a lane, an obstacle, and a movement of a parallel vehicle or an oncoming vehicle that affect a traveling direction of the vehicle, and performs processes such as development of a fixation for understanding the situation and checking of message information of the RTI (notification) as a return request. Furthermore, for example, in an urban area in which a road on which a pedestrian jumps and a school zone in which children jump out are mixed, a line-of-sight behavior for checking whether or not a person enters a road from a portion around the road is dominant.

A system that allows a human to temporarily accumulate information and process the information during an execution of a cognitive task is called a working memory (working storage). Then, information required for a determination of a human action is accumulated and processed in the working memory of a human. On the other hand, it is considered that there are restrictions on a capacity and a period for information accumulation. Specifically, the information accumulated in the working memory is faded with the lapse of time. For example, the information with low importance is first faded, and thus, the working memory operates like a dynamic cache memory. With spreading of the autonomous driving and improvement in performance of the autonomous driving, an available driving design range is extended. Thus, it is considered that a necessity for the user to constantly check the surrounding environment information required for safe manual driving is gradually reduced. Thereby, the number of times of forward checking required for traveling is reduced, or further the forward checking is not performed. Then, as work deviated from the driving steering work gradually increases, advance visual information of the traveling road required for determination decreases. Originally, a reason why the driver periodically performs a check of the forward road during the manual driving is that there is a weight stimulus of a risk importance that can be a risk factor. Therefore, the driver continuously executes advance visual search without neglect, and thus careless driving is prevented. On the other hand, in a case where work deviated from the driving steering work increases, there are few risk factors in the memory of the fading working memory. As a result, a necessity to periodically observe a change in the situation is reduced. Thus, observation of a behavior for making a line-of-sight of the driver toward the road and rechecking the situation is also reduced. In the present embodiment, in consideration of the characteristics of the human's working memory in which information with low risk importance as stored information is first faded over time, for the driver, information provision and a notification for the appropriate manual driving are performed at an appropriate timing. Thus, observation of a driver's state or a driver's response is performed.

Furthermore, in order for the driver to normally start actual manual driving in response to the RTI (notification) as a request for returning (switching) from the autonomous driving to the manual driving, a period for acquiring information required for an action determination is required. Furthermore, the visual information acquisition includes not only visual check as an action of acquiring the latest information but also an action of acquiring information for performing a feedback for an action control. Note that, in the present embodiment, as the information required for an action determination, for example, a human-machine interface such as means disclosed in Patent Document 5 filed by the present applicant can be used. For example, Patent Document 5 discloses a technique of dividing the traveling route into various sections (a manual driving section, a driver intervention requirement section, and the like) and displaying, to the driver, the traveling route in different colors and different line widths for each section. Furthermore, by devising a display time axis of approach information, the driver can visually know when the vehicle approaches each section requiring each measure with the lapse of time (=traveling of the host vehicle). That is, as described in Patent Document 5, the driver periodically updates and provides the approach information on a traveling course along the schedule of the vehicle. Thus, a fact that the vehicle approaches the takeover point over time is visually taken as into the working memory of thinking, as a risk. Thereby, the driver can grasp the imminent takeover approach information, as an imminent risk. In this way, provision of the visual approach information including semantic information corresponds to a stimulus for checking the situation before takeover assigned to the working memory. Then, a method of assigning the update information also affects the visual behavior of the driver. Therefore, in the present embodiment, in a case where the state of the driver is estimated from the eyeball behavior analysis and the observation evaluation value of the eyeball behavior, the observation behavior may be evaluated by incorporating information to be provided to the driver as an influence factor. By updating and presenting information from moment to moment by the human-to-machine interface, the driver recognizes importance of a necessity of a return from the autonomous driving to the manual driving with a sense of temporal approach. Thus, visual information required for returning is accumulated in the working memory of the driver. Then, in the action determination for returning of the driver, an action of acquiring insufficient information is executed before shifting to the action on the basis of the presented information and the emergency due to the driver's sense of risk. Therefore, by effectively inputting (storing) prediction information required for traveling in the working memory of the driver by the presentation information of the human-to-machine interface, and by appropriately providing information that makes the driver feel a necessity of rechecking on the way, it is possible to prevent the driver's unconsciousness from being significantly deviated. As a result, the determination of the driver is accelerated, and thus it is possible to reduce the return delay time of the driver (manual driving return possible time) disclosed in Patent Document 3.

In the present disclosure, the main focus is on the analysis of the eyeball behavior. On the other hand, in a case where the awakening state of the driver is insufficient, the feedback of the acquired information described above may be incompletely performed. As a result, various behaviors and the like appear in addition to the eyeball behavior, and this may lead to excessive steering of the driver in some cases. Therefore, the eyeball behavior with respect to the RTI (notification) as a return request differs between the driver who uses the autonomous driving function while periodically checking the prediction information for predicting a situation of a point at which the autonomous driving is switched to the manual driving and the driver who completely neglects such periodic checking. Moreover, in a case where a time required for the driver to return to the manual driving is not enough and the driver shifts to a steering action with incomplete understanding of the situation for the manual driving, a feedback in the steering action tends to be incomplete, and overshoot steering with an inappropriate steering amount such as excessive steering may occur.

Therefore, in order to appropriately function the estimation of the return reaction level (awakening level) and the return delay time of the driver by the analysis of the eyeball behavior, the vehicle control system 100 according to the embodiment of the present disclosure is configured as a system that determines a return action of the driver by mutual influences of approach information presented with traveling of the vehicle by the driver, additional information added to risk information to be presented, a notification for the driver, an actual return action and an eyeball behavior induced by the notification, a steering stability as a result of the return action, and the like.

6.5 Information Processing Method

Figure 10:
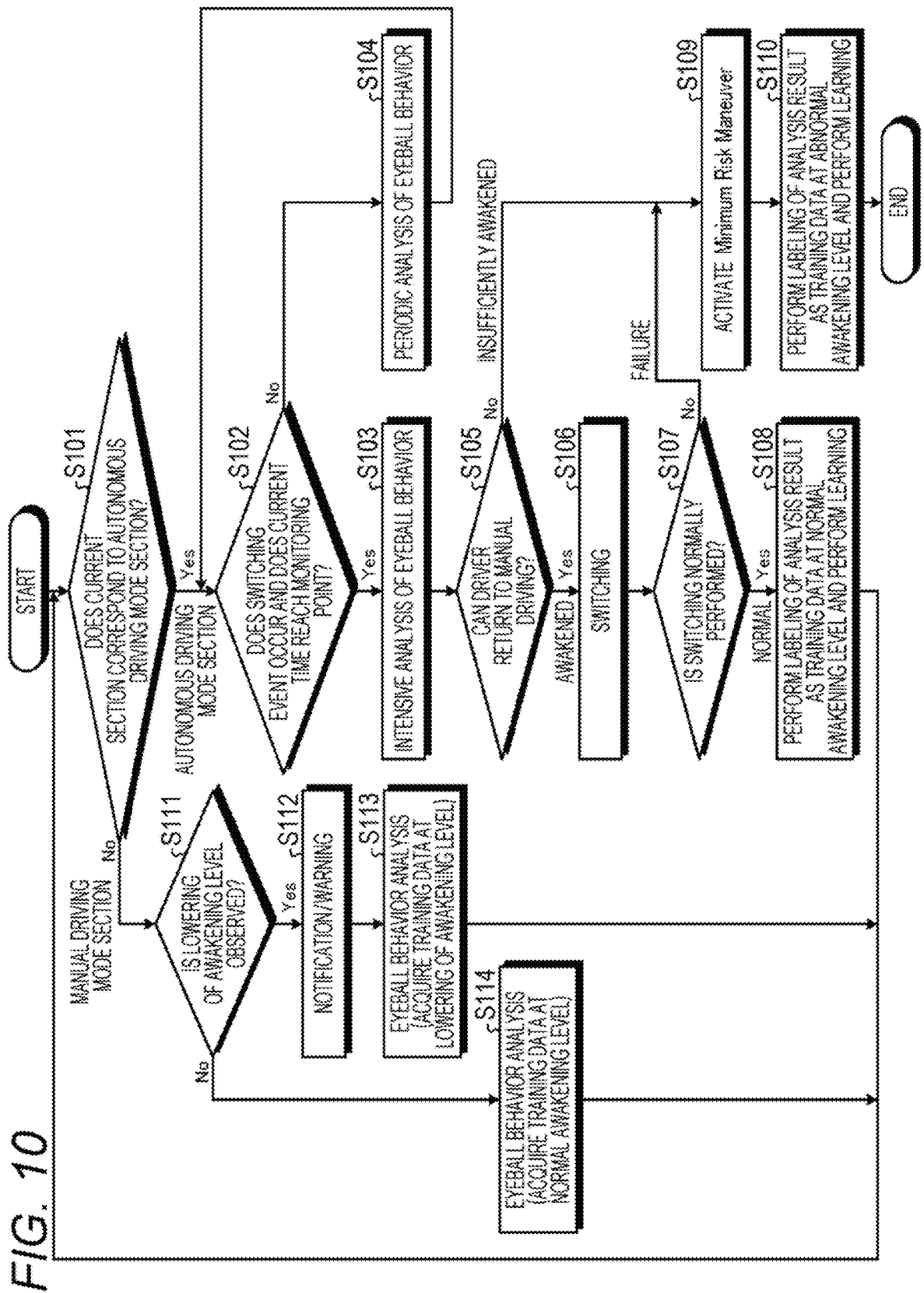
FIG. 10 is a flowchart of an information processing method according to the embodiment of the present disclosure.

Next, an information processing method according to the embodiment of the present disclosure will be described with reference to FIG. 10. Here, a description will be given focusing on acquisition of the training data. FIG. 10 is a flowchart of an information processing method according to the embodiment of the present disclosure. Specifically, as illustrated in FIG. 10, the information processing method according to the present embodiment can include steps from step S101 to step S114. Details of each of these steps according to the present embodiment will be described below.

First, the vehicle control system 100 determines whether or not a current section corresponds to an autonomous driving mode section (step S101). The vehicle control system 100 proceeds to processing of step S102 in a case where a current section corresponds to an autonomous driving mode section (Yes in step S101), and proceeds to processing of step S111 in a case where a current section does not correspond to an autonomous driving mode section (that is, a manual driving mode section) (NO in step S101).

Here, the description will be mainly given focusing on observation and analysis of the eyeball behavior. In the autonomous driving mode section, the vehicle control system 100 periodically performs various observations for estimating a position, a posture, and activity content of the driver before awakening and predicting a required time for which the driver returns to the return correspondence level (awakening level) at which the manual driving is allowed (passive monitoring). Then, the vehicle control system 100 determines whether or not a switching event of the driving mode occurs and whether or not a current time reaches a preset monitoring point on the basis of information predicted at a timing when the event occurs (step S102). In a case where a switching event of the driving mode occurs and a current time reaches a preset monitoring point (Yes in step S102), the vehicle control system 100 proceeds to processing of step S103. On the other hand, in a case except the case where a switching event of the driving mode occurs and a current time reaches a preset monitoring point (NO in step S102), the vehicle control system 100 proceeds to processing of step S104.

Next, in accordance with the switching of the driving mode, the vehicle control system 100 performs, for the driver, an RTI (notification) as a request for a return to an initial stage, detects that the driver is seated on the driver's seat, observes a posture (a direction of a body or a face) and the like of the driver, and intensively executes eyeball behavior analysis at a high frame rate (step S103). Here, one purpose of performing eyeball behavior analysis is to estimate an activity amount in a brain of the driver and check whether or not the driver returns to the return correspondence level (awakening level) at which the manual driving is allowed immediately before switching to the manual driving mode. This sampling and analysis of the eyeball behavior are performed in a limited period on the basis of a captured image in a narrow area including only a face and an eyeball of the driver seating on the driver's seat. At this time, in addition to the eyeball behavior analysis at a high frame rate, the vehicle control system 100 may intensively perform active monitoring including a notification, a warning, or a question (question that involves cognition and determination for a response, such as a question in a quiz format) and detection of a response to the notification, the warning, or the question (an utterance, a gesture, a manual input, a movement of a line-of-sight, or the like), input of a pseudo R steering, and detection of viewing of display information provided by the vehicle control system 100, and the like. Furthermore, the vehicle control system 100 may detect objects to be viewed, a viewing order of the objects, torque input to a steering wheel, a pressing action on a brake pedal, a pressing action on an accelerator pedal, and the like. By performing such detection, it is possible to detect whether or not the driver appropriately performs a return procedure to the manual driving. Moreover, the active monitoring may be performed simultaneously with the eyeball behavior analysis at a high frame rate or may be performed with a time difference.

Furthermore, the vehicle control system 100 periodically executes passive monitoring including, for example, eyeball behavior analysis at a low frame rate (step S104). Note that, in the flowchart of FIG. 10, passive monitoring including eyeball behavior analysis is executed. On the other hand, the present embodiment is not limited thereto, and passive monitoring not including eyeball behavior analysis may be periodically executed. Note that, in step S104, it is preferable that the vehicle control system 100 continuously observes a change leading to an event requiring switching from the autonomous driving to the manual driving and appropriately changes monitoring content, a monitoring timing, a monitoring cycle, and the like according to the change. Note that details of step S104 will be described later.

Next, the vehicle control system 100 detects the awakening level of the driver on the basis of the result of the eyeball behavior analysis in step S103 described above, and further determines the return correspondence level as to whether or not the driver can return to the manual driving (step S105). The vehicle control system 100 proceeds to processing of step S106 in a case where it is determined that the driver is sufficiently awakened and can return to the manual driving (Yes in step S105), and proceeds to processing of step S109 in a case where it is determined that the driver is insufficiently awakened and cannot return to the manual driving (No in step S105).

Next, the vehicle control system 100 executes switching from the autonomous driving mode to the manual driving mode (step S106). Moreover, the vehicle control system 100 determines whether or not the switching is normally performed (step S107). The vehicle control system 100 proceeds to processing of step S108 in a case where the switching is normally performed (normal) (Yes in step S107), and proceeds to processing of step S109 in a case where the switching is not normally performed (failure) (No in step S107).

Next, the vehicle control system 100 labels the result of the eyeball behavior analysis in step S103 described above, as training data when the awakening level is normal, performs learning (step S108), and returns to processing of step S101.

Next, the vehicle control system 100 activates the MRM (step S109). Moreover, the vehicle control system 100 labels the result of the eyeball behavior analysis in step S103 described above, as training data when the awakening level is abnormal, performs learning (step S110), and ends the processing.

Next, the vehicle control system 100 determines whether or not lowering of the awakening level of the driver is observed (step S111). The vehicle control system 100 proceeds to processing of step S112 in a case where lowering of the awakening level of the driver is observed (Yes in step S111), and proceeds to processing of step S114 in a case where lowering of the awakening level of the driver is not observed (No in step S111). Note that, in the present embodiment, in the manual driving mode section, it is preferable to periodically perform observation for estimating the awakening level of the driver according to the autonomous driving level or the like.

Next, the vehicle control system 100 performs a notification and a warning for the driver (active monitor) (step S112). Moreover, the vehicle control system 100 executes eyeball behavior analysis at a high frame rate, labels the result of the eyeball behavior analysis, as training data when the awakening level is lowered, performs learning (step S113), and returns to processing of step S101.

Next, the vehicle control system 100 executes eyeball behavior analysis, labels the result of the eyeball behavior detailed analysis, as training data when the awakening level is normal, performs learning (step S114), and returns to processing of step S101.

Figure 11:
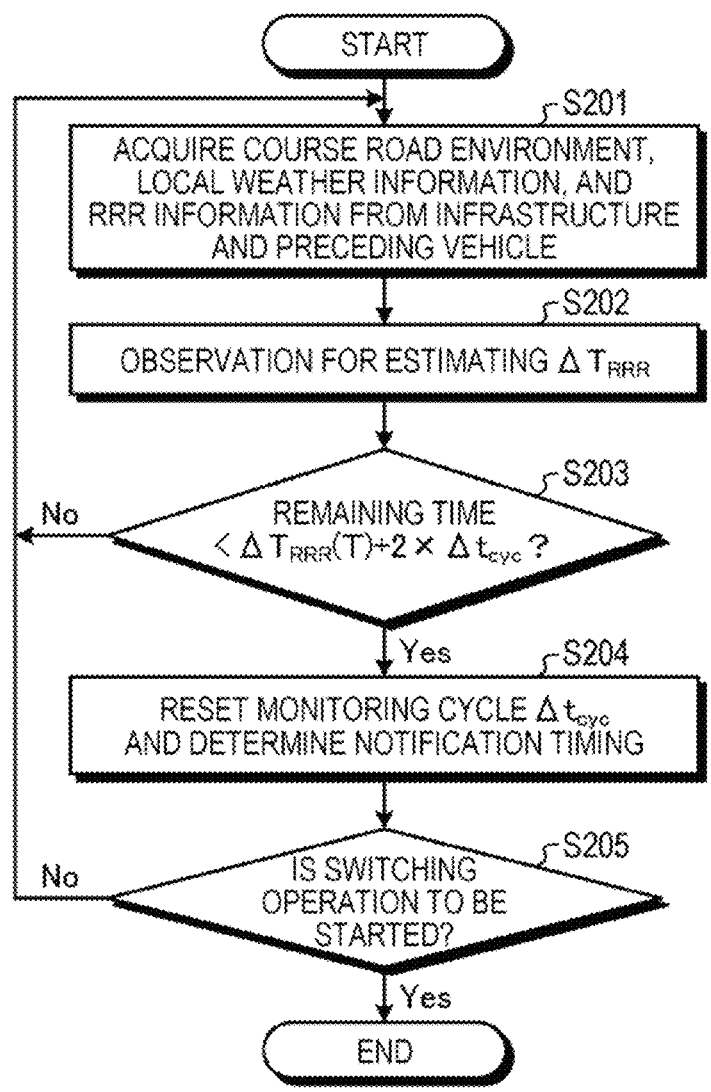
FIG. 11 is a sub-flowchart of step S104 illustrated in FIG. 10.

Next, details of step S104 described above will be described with reference to FIG. 11. FIG. 11 is a sub-flowchart of step S104 illustrated in FIG. 10. Specifically, as illustrated in FIG. 11, the information processing method according to the present embodiment can include steps from step S201 to step S205. Details of each of these steps will be described below.

First, the vehicle control system 100 acquires a course road environment, local weather information, and RRR information such as a predetermined RRR from an infrastructure and a preceding vehicle (step S201). Here, the requested recovery rate (RRR) refers to a predetermined success rate at which the driver is expected to appropriately start the manual driving at a point where switching from the autonomous driving to the manual driving is performed, the point being determined on the basis of the LDM or the like. Furthermore, it is assumed that an estimated extension time (manual driving return possible time) for allowing switching with the RRR at an arrival timing of the switching point from the autonomous driving to the manual driving is defined as $\Delta T_{RRR}$ (T) (note that the estimated extension time is disclosed in Patent Document 3 as a return delay time). That is, when $\Delta T_{RRR}$ (T) elapses from the RTI (notification) as a return request, the driver is expected to appropriately return to the manual driving with a success rate of the RRR. Note that the RRR is embedded information assigned to each section of the road. For example, the vehicle control system 100 can acquire the RRR from the infrastructure together with the update information of the LDM. Furthermore, the RRR may be appropriately changed and set from numerical values assigned to each section by attribute information of the driver (a driving experience, a driving skill, and the like) and the like. More specifically, for example, in a case where switching to the manual driving cannot be performed due to a narrow main road or the like and the vehicle stops at the corresponding section, when the vehicle may cause road closure or traffic congestion, the RRR assigned to the section is set to 100% (that is, it is required to reliably perform switching to the manual driving in the section). On the other hand, for example, in a case where switching to the manual driving cannot be performed because the road is a country road with very little traffic and the vehicle stops at the corresponding section, when the vehicle does not cause road closure or traffic congestion, the RRR assigned to the section may be set to a low value such as 50% (that is, it is not required to reliably perform switching to the manual driving in the section). Furthermore, the estimated extension time $\Delta T_{RRR}$ (T) can be calculated on the basis of the set RRR, an attribute (a driving experience, a driving skill, and the like) and a state (content of a secondary task, an awakening level, a physical condition, a posture, and the like) of the driver.

Next, it is checked that the driver returns to the driver's seat by a notification at a first stage that is included in the RTIs (notifications) as multi-stage return requests, the vehicle control system 100 starts observation for estimating $\Delta T_{RRR}$ (T) (step S202).

Next, the vehicle control system 100 compares a remaining time until the host vehicle reaches a point (takeover limit point) at which switching from the autonomous driving to the manual driving is performed with a predetermined time (step S203). Specifically, in a case where an observation timing $T_{ob1}$ when observation is executed last has passed a timing $T_{bac}$ which is returned by a time $\Delta T_{RRR} + \Delta T_{cyc}$ from a timing when the takeover limit point is reached, an observation timing $T_{ob2}$ when next observation is to be executed has passed a timing $T_{nt}$ which is returned by a time $\Delta T_{RRR}$ from a timing when the takeover limit point is reached (note that $\Delta T_{cyc}$ is an observation cycle). In this case, the observation timing $T_{ob2}$ has passed the timing $T_{nt}$ when a notification should be performed, and as a result, a timing when the RTI (notification) as a return request is to be performed for the driver is missed. Therefore, in the present embodiment, in step S203 described above, the vehicle control system 100 compares the remaining time with $\Delta T_{RRR} + 2 \times \Delta T_{cyc}$ (predetermined time), and examines the observation cycle $\Delta T_{cyc}$ according to the comparison result. Thereafter, the vehicle control system 100 performs observation several times, or determines a timing of the RTI (notification) as a return request.

More specifically, the vehicle control system 100 proceeds to processing of step S204 in a case where the remaining time is shorter than $\Delta T_{RRR} + 2 \times \Delta T_{cyc}$ (Yes in step S203), and returns to processing of step S201 in a case where the remaining time is longer than $\Delta T_{RRR} + 2 \times \Delta T_{cyc}$ (No in step S203).

The vehicle control system 100 resets the observation cycle $\Delta T_{cyc}$ to be shorter, and then performs observation several times or changes observation means capable of more accurately determining the return correspondence level (awakening level) (step S204). Note that the present embodiment is not limited to the examination of the observation cycle $\Delta T_{cyc}$ based on the remaining time and the change of the observation means. For example, in a case where an event of switching from the autonomous driving mode to the manual driving mode newly occurs, the observation cycle $\Delta T_{cyc}$ may be examined or the observation means may be changed. Furthermore, in the present embodiment, for example, in a case where the RRR is changed due to a change in traffic volume at a point (takeover limit point) at which switching from the autonomous driving to the manual driving is performed, a change in accident occurrence probability due to the change in traffic, a degree of embedding of an evacuation parking space, and the like, the observation cycle $\Delta T_{cyc}$ may be examined or the observation means may be changed when the RRR is changed. Moreover, in the present embodiment, for example, in a case where the RRR is changed on the basis of the awakening level of the driver or content of a non-driving related activity (NDRA) such as a secondary task, the observation cycle $\Delta T_{cyc}$ may be examined or the observation means may be changed. Furthermore, in the present embodiment, the observation means may be changed on the basis of factors (a straight road, a mixed traffic, road surface freezing, and complexity risk information) that complicate situation recognition executed in a case where the driver performs the manual driving.

Moreover, in the present embodiment, the vehicle control system 100 determines a timing when the RTI (notification) as a return request is performed (step S204). In the present embodiment, for example, the notification timing may be changed on the basis of the awakening level of the driver, the content of NDRA such as a secondary task, the position and the posture of the driver, and the like (for example, in a case where the awakening level is low, the notification timing is set to be earlier). Moreover, the present embodiment is not limited thereto. For example, the notification timing may be changed in a case where the RRR is changed due to an occurrence of a new event of switching from the autonomous driving mode to the manual driving mode, a change in traffic volume at the takeover limit point, a change in the accident occurrence probability due to the change in traffic, a degree of embedding of the evacuation parking space, or the like. Note that, in a case where a notification is performed immediately before switching from the autonomous driving to the manual driving, depending on the state of the driver, a time required for the driver to return to the manual driving may not be enough, and switching at the takeover limit point (a start of the manual driving) may be difficult. On the other hand, in a case where a notification is early performed, the driver's consciousness related to importance for a necessity to start a switching action (takeover action) from the autonomous driving to the manual driving becomes low. As a result, it is considered that preparation for switching to the manual driving may be neglected. Therefore, in the present embodiment, it is required to perform the RTI (notification) as a return request at an optimum timing. Furthermore, in the present embodiment, the notification may be performed a plurality of times.

Next, the vehicle control system 100 determines whether to start an operation for switching from the autonomous driving mode to the manual driving mode (step S205). In a case where it is determined that the operation is to be started (Yes in step S205), the vehicle control system 100 ends step S104 to start the operation, and proceeds to processing of step S102 in FIG. 10. On the other hand, in a case where it is determined that the operation is not to be started (No in step S205), the vehicle control system 100 returns to processing of step S201.

As described above, in the present embodiment, the analysis result of the eyeball behavior specified for each driver during traveling is acquired, learning is performed, and the awakening level (return reaction level) of the driver is determined with reference to the eyeball behavior that is specified for each driver and is obtained on the basis of such learning. As a result, according to the present embodiment, it is possible to improve an accuracy of the determination.

6.6 Summary

As described above, according to the embodiment of the present disclosure, it is possible to accurately determine the awakening level (return reaction level) of the driver while reducing a load in imaging processing, analysis processing, and the like.

Note that, in the embodiment of the present disclosure, a vehicle has been described as an example. On the other hand, the present embodiment is not limited to the example applied to a vehicle, and may be applied to a moving object such as a vehicle, an electric vehicle, a hybrid electric vehicle, a motorcycle, a personal mobility, an airplane, a ship, a construction machine, and an agricultural machine (tractor).

7. Hardware Configuration

Figure 12:
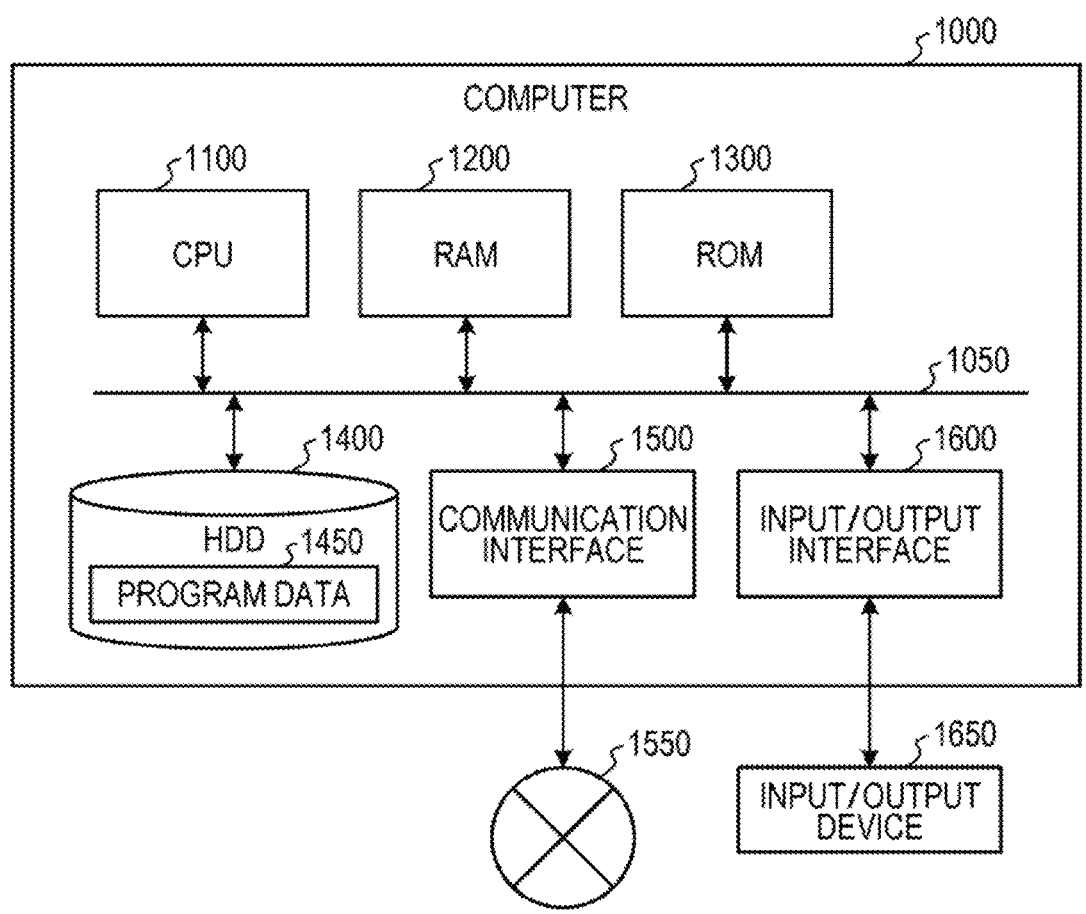
FIG. 12 is a hardware configuration diagram illustrating an example of a computer 1000 that realizes some functions of the vehicle control system 100.

A part of the vehicle control system 100 according to each embodiment described above is realized, for example, by a computer 1000 with a configuration as illustrated in FIG. 12. FIG. 12 is a hardware configuration diagram illustrating an example of a computer 1000 that realizes some functions of the vehicle control system 100. The computer 1000 includes a CPU 1100, a RAM 1200, a read only memory (ROM) 1300, a hard disk drive (HDD) 1400, a communication interface 1500, and an input/output interface 1600. The units of the computer 1000 are connected to each other by a bus 1050.

The CPU 1100 operates on the basis of a program stored in the ROM 1300 or the HDD 1400, and controls each unit. For example, the CPU 1100 develops a program stored in the ROM 1300 or the HDD 1400 into the RAM 1200, and executes processing corresponding to various programs.

The ROM 1300 stores a boot program such as a basic input output system (BIOS) to be executed by the CPU 1100 in a case where the computer 1000 is started, a program depending on hardware of the computer 1000, and the like.

The HDD 1400 is a non-transitory computer-readable recording medium that records a program to be executed by the CPU 1100, data to be used by the program, and the like. Specifically, the HDD 1400 is a recording medium that records an information processing program according to the present disclosure as an example of program data 1450.

The communication interface 1500 is an interface for connecting the computer 1000 to an external network 1550 (for example, the Internet). For example, the CPU 1100 receives data from another apparatus or transmits data generated by the CPU 1100 to another apparatus via the communication interface 1500.

The input/output interface 1600 is an interface for connecting an input/output device 1650 and the computer 1000. For example, the CPU 1100 receives data from the input/output device 1650 such as a keyboard, a mouse, and a microphone (microphone) via the input/output interface 1600. Furthermore, the CPU 1100 transmits data to an output device such as a display, a speaker, or a printer via the input/output interface 1600. Furthermore, the input/output interface 1600 may function as a media interface that reads a program or the like recorded in a predetermined recording medium (medium). The medium is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, in a case where the computer 1000 functions as a part of the vehicle control system 100 according to the embodiment of the present disclosure, the CPU 1100 of the computer 1000 realizes the functions of the autonomous driving control unit 112 and the like by executing a program stored in the RAM 1200. Furthermore, the HDD 1400 stores an information processing program and the like according to the present disclosure. Note that the CPU 1100 reads the program data 1450 from the HDD 1400 and executes the program data. On the other hand, as another example, these programs may be acquired from another apparatus via the external network 1550.

Furthermore, the autonomous driving control unit 112 and the like according to the present embodiment may be applied to, for example, a system including a plurality of apparatuses on a premise of connection to a network (or communication between apparatuses), such as cloud computing. That is, the information processing apparatus according to the present embodiment described above can be realized, for example, as the information processing system according to the present embodiment by the plurality of apparatuses. An example of the hardware configuration of a part of the vehicle control system 100 has been described above. Each of the above-described components may be configured using a general-purpose member, or may be configured by hardware specialized for the function of each component. Such a configuration can be appropriately changed according to a technical level at the time of implementation.

8. Supplement

Note that the embodiment of the present disclosure described above may include, for example, the information processing method executed by the information processing apparatus or the information processing system as described above, a program for causing the information processing apparatus to function as a vehicle control system, and a non-transitory tangible medium in which the program is recorded. Furthermore, the program may be distributed via a communication line (including wireless communication) such as the Internet.

Furthermore, each step in the information processing method according to the embodiment of the present disclosure described above may not be necessarily performed in the described order. For example, each step may be performed in an appropriately-changed order. Furthermore, some steps may be performed in parallel or individually instead of being performed in time series. Moreover, processing of each step may not necessarily have to be performed according to the described method, and may be performed, for example, by another method via another functional unit.

Note that, in the description of the embodiment of the present disclosure described above, it is assumed that the image capturing device is controlled by fixing or varying an operation frame rate. On the other hand, a concept of the frame rate may not necessarily exist in an image capturing device of a type called an event-driven imaging device, an event-based imaging device, a neuromorphic retina, or an event camera. These event-driven imaging devices are an image capturing device of a type that converts an occurrence time and a coordinate of a quantization change into a signal on the basis of an impulse recognized as a change in brightness and records the signal. In an image capturing control of the event-driven imaging device, in a case where a change in information to be captured as light occurs vigorously in the entire screen, an amount of information processing executed in parallel becomes excessive, and the processing amount is increased. As a result, a rise in operation temperature of the device, an excessive number of events occurring simultaneously and in parallel, and the like may occur. Therefore, in a case where the state of the driver is observed using these event-driven imaging devices in which the concept of the frame rate does not exist, in order to optimize a detection frequency of the event (change) by the event-driven imaging device during the observation period for evaluation, preferably, the following step is performed. In the present embodiment, for example, in order to adjust lighting brightness of a lighting device that lights the driver with light having a wavelength in a narrow infrared wavelength region, a light-receiving conversion gain or a quantization threshold value for detection of an event (change) is adjusted. By performing the adjustment, it is possible to execute observation such as detection of the eyeball behavior such as a microsaccade and a drift of an eyeball, detection of a blink, or observation of a change in expression of a face at an optimum frequency in order to recognize the change as an observation target, while suppressing an increase in the processing amount. That is, in a case where the event-driven imaging device is used, switching of the analysis mode according to the embodiment of the present disclosure can be performed by controlling a threshold value or the like.

Furthermore, in the description of the embodiment of the present disclosure, the embodiment has been described in detail on the basis of the autonomous driving levels defined by the SAE. On the other hand, the concept of classifying use of the autonomous driving by the autonomous driving levels is a classification classified by a design viewpoint of a vehicle. On the other hand, from the user's viewpoint, it is not necessarily easy for the driver to drive a vehicle according to an autonomous driving level of available autonomous driving levels of the vehicle after the user always correctly understands and grasps the autonomous driving levels in a driving design range in which driving according to each level of the autonomous driving levels is allowed. That is, the design may be referred to as machine centered design in which a vehicle is used according to a function or an instruction of a machine. That is, in a case where a correspondence situation of the vehicle system dynamically changes with time due to various external factors and internal factors and the autonomous driving level in traveling is not uniquely determined only in a physical road section and the like, it can be said that the driver is required to dependently cope with the level allowed by the road situation determined by the vehicle control system 100 each time. On the other hand, in a case where a relationship between the driver and the vehicle control system 100 is viewed from an ergonomic viewpoint, in order to achieve the purpose of using the vehicle such as a movement and obtain secondary advantages obtained during the movement, the user performs action determination in consideration of balance between a burden of driving and various risks caused by the driving. Here, the burden refers to vehicle steering work for movement and a certain risk caused by the work. Originally, an advantage of the autonomous driving from the driver's viewpoint is that a restraint by driving is released and a time for driving can be used for a meaningful time which is not related to driving and can be used without being dependent on driving. In order to provide such advantages, it can be said that it is necessary to convert an idea supporting the autonomous driving control to an idea called a human centered design obtained by reversing a relationship in the idea called the machine centered design in the related art. Then, in a case of examining a relationship between the vehicle control system 100 of the vehicle and the driver as a user on the basis of the viewpoint of such an idea, it can be said that use of autonomous driving is a desirable use form from an ergonomic viewpoint, the autonomous driving being used for allowing actual various autonomous driving functions according to an awakening state and a physical preparation situation of the driver in correspondence with available autonomous driving levels in a "driving design range" as a design of the vehicle.

A human performs his/her action selection while maintaining a balance between a selectable benefit and a loss or a risk involved with the benefit, and further learns the action. By introducing a control based on the human centered design, action learning is performed such that the driver can prepare for an appropriate return according to an upper limit of an autonomous driving steering environment allowed for each road on which the driver drives the vehicle. Moreover, for a driver for whom such action learning is performed, the driver is allowed to leave at a higher level such as the autonomous driving level 4 or the like, that is, to leave from the driving steering work by advanced autonomous driving traveling that can obtain a benefit of performing NDRA or the like. On the other hand, in a case where a state indicating an expected appropriate return of the driver cannot be observed, or in a case where the return level is lowered on the basis of the observation state of the driver with reference to a past return response history or the learning data of the driver, even within the "design driving range", by prohibiting use of the autonomous driving level 4 or the like at which the driver can leave the driving steering work or limiting use of the autonomous driving level 3 to a short time, use of the autonomous driving may be greatly limited.

That is, instead of allowing the autonomous driving level determined as the "driving design range" from a performance criterion of a sensing device provided in the vehicle and a performance criterion of the determination processing, the autonomous driving control that allows use of autonomous driving based on a correspondence ability of a human is a form of vehicle use which is easy to a human. That is, by converting a control concept of the autonomous driving system of the vehicle from the concept called machine centered design to human centered design, it is possible to provide a use form which is easy to a human by the autonomous driving control. Then, in the description of the present disclosure, an applicable control using the state observation means of the driver has been described on the basis of the former machine centered design. On the other hand, even in a case where the control concept is replaced with human centered design, a switching action of the driver (takeover action) from the autonomous driving to the manual driving similarly occurs. Thus, the applicable control using the state observation means of the driver described above can be performed.

As described above, the preferred embodiment of the present disclosure has been described in detail with reference to the accompanying drawings. On the other hand, the technical scope of the present disclosure is not limited to such examples. It is understood by those skilled in the technical field of the present disclosure that various modifications and various changes may be made within the scope of the technical idea described in the claims and such modifications or changes fall within the scope and spirit of the present disclosure.

Furthermore, the effects described in the present specification are merely illustrative or exemplary, and are not restrictive. That is, the technique according to the present disclosure can exhibit other effects obvious to those skilled in the art from the description of the present specification together with or instead of the above effects.

Note that the following configurations also fall within the technical scope of the present disclosure.

(1)

An information processing apparatus including:

an eyeball behavior analysis unit that analyzes an eyeball behavior of a driver who drives a moving object, in which the eyeball behavior analysis unit dynamically switches an analysis mode according to a driving mode of the moving object.

(2)

The information processing apparatus according to (1), in which the eyeball behavior includes at least one of a saccade, a fixation, or a microsaccade of an eyeball.

(3)

The information processing apparatus according to (1) or (2), in which the eyeball behavior analysis unit performs switching between at least a first analysis mode and a second analysis mode, performs analysis at a first frame rate in the first analysis mode, and performs analysis at a second frame rate lower than the first frame rate in the second analysis mode.

(4)

The information processing apparatus according to (3), in which the eyeball behavior analysis unit performs analysis in the first analysis mode, in a driving mode change preparation mode in which the driving mode of the moving object is switched from an autonomous driving mode to a manual driving mode.

(5)

The information processing apparatus according to (4), in which a start point of the first analysis mode is determined on the basis of at least one of a schedule, a local dynamic map, or state information of the driver.

(6)

The information processing apparatus according to (4) or (5), further including: a determination unit that determines a return correspondence level to manual driving of the driver on the basis of an analysis result of an eyeball behavior of the driver in the first analysis mode.

(7)

The information processing apparatus according to (6), in which the determination unit determines the return correspondence level by comparing the analysis result of the eyeball behavior of the driver in the first analysis mode with an analysis result of the eyeball behavior of the driver that is previously acquired.

(8)

The information processing apparatus according to (7), further including: a learning device that generates a database for the determination by learning the analysis result of the eyeball behavior of the driver that is previously acquired.

(9)

The information processing apparatus according to any one of (6) to (8), further including: a moving object driving control unit that switches the driving mode of the moving object on the basis of a determination result of the return correspondence level.

(10)

The information processing apparatus according to any one of (4) to (9), in which the eyeball behavior analysis unit performs analysis in the second analysis mode in a case where the driving mode of the moving object is the autonomous driving mode.

(11)

The information processing apparatus according to (10), in which the eyeball behavior analysis unit dynamically switches an analysis frequency according to an autonomous driving level in the autonomous driving mode.

(12)

The information processing apparatus according to any one of (4) to (11), in which the eyeball behavior analysis unit performs analysis in the first analysis mode or the second analysis mode in a case where the driving mode of the moving object is the manual driving mode.

(13)

The information processing apparatus according to any one of (4) to (12), in which the eyeball behavior analysis unit performs analysis in the first analysis mode according to lowering of an awakening level of the driver.

(14)

An information processing system including:

an eyeball behavior analysis unit that analyzes an eyeball behavior of a driver who drives a moving object, in which the eyeball behavior analysis unit dynamically switches an analysis mode according to a driving mode of the moving object.

(15)

The information processing system according to (14), further including: a monitoring unit that monitors the eyeball behavior of the driver.

(16)

An information processing method including:

analyzing, via an eyeball behavior analysis unit, an eyeball behavior of a driver who drives a moving object, in which an analysis mode of the analysis is dynamically switched according to a driving mode of the moving object.

(17)

An information processing program causing a computer to execute:

an analysis function of analyzing an eyeball behavior of a driver who drives a moving object, in which an analysis mode of the analysis function is dynamically switched according to a driving mode of the moving object.

| REFERENCE SIGNS LIST | |
|---|---|
| 100 | Vehicle control system |
| 101 | Input unit |
| 102 | Data acquisition unit |
| 103 | Communication unit |
| 104 | In-vehicle device |
| 105 | Output control unit |
| 106 | Output unit |
| 107 | Drive system control unit |
| 108 | Drive system |
| 109 | Body system control unit |
| 110 | Body system |
| 111 | Storage unit |
| 112 | Autonomous driving control unit |
| 113 | Sensor unit |
| 121 | Communication network |
| 131 | Detection unit |
| 132 | Self-position estimation unit |
| 133 | Situation analysis unit |
| 134 | Planning unit |

-continued

| REFERENCE SIGNS LIST | |
|---|---|
| 135 | Operation control unit |
| 141 | Outer-vehicle information detection unit |
| 142 | In-vehicle information detection unit |
| 143 | Vehicle state detection unit |
| 151 | Map analysis unit |
| 152 | Traffic rule recognition unit |
| 153 | Situation recognition unit |
| 154 | Situation prediction unit |
| 161 | Route planning unit |
| 162 | Action planning unit |
| 163 | Operation planning unit |
| 171 | Emergency avoidance unit |
| 172 | Acceleration/deceleration control unit |
| 173 | Direction control unit |
| 200 | Position/posture detection unit |
| 202 | Face recognition unit |
| 204 | Face tracking unit |
| 206 | Eyeball tracking unit |
| 208 | Biometric information detection unit |
| 210 | Authentication unit |
| 300 | Eyeball behavior analysis unit |
| 302 | Eyeball behavior learning device |
| 310 | Database |
| 320 | Determination unit |

The invention claimed is:

1. An information processing apparatus comprising:
an eyeball behavior analysis unit that analyzes an eyeball behavior of a driver who drives a moving object, wherein the eyeball behavior analysis unit dynamically switches between at least a first analysis mode and a second analysis mode according to a driving mode of the moving object, wherein
the eyeball behavior analysis unit
performs analysis at a first frame rate in the first analysis mode, and
performs analysis at a second frame rate, lower than the first frame rate, in the second analysis mode;
the eyeball behavior analysis unit performs analysis in the first analysis mode based on the driving mode being a driving mode change preparation mode in which the driving mode of the moving object is switched from an autonomous driving mode to a manual driving mode; and
a determination unit that determines a return correspondence level to manual driving of the driver on a basis of an analysis result of the eyeball behavior of the driver in the first analysis mode, wherein the determination unit determines the return correspondence level by comparing the analysis result of the eyeball behavior of the driver in the first analysis mode with an analysis result of the eyeball behavior of the driver that is previously acquired.

2. The information processing apparatus according to claim 1, wherein the eyeball behavior includes at least one of a saccade, a fixation, or a microsaccade of an eyeball.

3. The information processing apparatus according to claim 1, wherein a start point of the first analysis mode is determined on a basis of at least one of a schedule, a local dynamic map, or state information of the driver.

4. The information processing apparatus according to claim 1, further comprising: a learning device that generates a database for the determination by learning the analysis result of the eyeball behavior of the driver that is previously acquired.

5. The information processing apparatus according to claim 1, further comprising: a moving object driving control unit that switches the driving mode of the moving object on a basis of a determination result of the return correspondence level.

6. The information processing apparatus according to claim 1, wherein the eyeball behavior analysis unit performs analysis in the second analysis mode in a case where the driving mode of the moving object is the autonomous driving mode.

7. The information processing apparatus according to claim 6, wherein the eyeball behavior analysis unit dynamically switches an analysis frequency according to an autonomous driving level in the autonomous driving mode.

8. The information processing apparatus according to claim 1, wherein the eyeball behavior analysis unit performs analysis in the first analysis mode or the second analysis mode in a case where the driving mode of the moving object is the manual driving mode.

9. The information processing apparatus according to claim 1, wherein the eyeball behavior analysis unit performs analysis in the first analysis mode according to lowering of an awakening level of the driver.

10. An information processing system comprising:
an eyeball behavior analysis unit that analyzes an eyeball behavior of a driver who drives a moving object, wherein the eyeball behavior analysis unit dynamically switches between at least a first analysis mode and a second analysis mode according to a driving mode of the moving object, wherein
the eyeball behavior analysis unit
performs analysis at a first frame rate in the first analysis mode, and
performs analysis at a second frame rate, lower than the first frame rate, in the second analysis mode;
the eyeball behavior analysis unit performs analysis in the first analysis mode based on the driving mode being a driving mode change preparation mode in which the driving mode of the moving object is switched from an autonomous driving mode to a manual driving mode; and
a determination unit that determines a return correspondence level to manual driving of the driver on a basis of an analysis result of the eyeball behavior of the driver in the first analysis mode, wherein the determination unit determines the return correspondence level by comparing the analysis result of the eyeball behavior of the driver in the first analysis mode with an analysis result of the eyeball behavior of the driver that is previously acquired.

11. The information processing system according to claim 10, further comprising: a monitoring unit that monitors the eyeball behavior of the driver.

12. An information processing method comprising:
analyzing, via an eyeball behavior analysis unit, an eyeball behavior of a driver who drives a moving object;
dynamically switching an analysis mode of the eyeball behavior analysis unit between at least a first analysis mode and a second analysis mode according to a driving mode of the moving object;
performing analysis at a first frame rate in the first analysis mode;
performing analysis at a second frame rate, lower than the first frame rate, in the second analysis mode;
performing analysis in the first analysis mode based on the driving mode being a driving mode change preparation mode in which the driving mode of the moving object is switched from an autonomous driving mode to a manual driving mode; and determining a return correspondence level to manual driving of the driver on a basis of an analysis result of the eyeball behavior of the driver in the first analysis mode, wherein the return correspondence level is determined by comparing the analysis result of the eyeball behavior of the driver in the first analysis mode with an analysis result of the eyeball behavior of the driver that is previously acquired.

13. A non-transitory computer-readable recording medium storing instructions which, when processed by a processor, cause the processor to implement a method comprising:

analyzing an eyeball behavior of a driver who drives a moving object, dynamically switching an analysis mode used for analyzing the eyeball behavior between at least a first analysis mode and a second analysis mode according to a driving mode of the moving object, performing analysis at a first frame rate in the first analysis mode;

performing analysis at a second frame rate, lower than the first frame rate, in the second analysis mode;

performing analysis in the first analysis mode based on the driving mode being a driving mode change preparation mode in which the driving mode of the moving object is switched from an autonomous driving mode to a manual driving mode; and determining a return correspondence level to manual driving of the driver on a basis of an analysis result of the eyeball behavior of the driver in the first analysis mode, wherein the return correspondence level is determined by comparing the analysis result of the eyeball behavior of the driver in the first analysis mode with an analysis result of the eyeball behavior of the driver that is previously acquired.

* * * * *